US010266809B2

(12) United States Patent
Rowan et al.

(10) Patent No.: US 10,266,809 B2
(45) Date of Patent: Apr. 23, 2019

(54) POLYMER SUITABLE FOR USE IN CELL CULTURE (71) Applicant: STICHTING KATHOLIEKE UNIVERSITEIT, Nijmegen (NL)

(72) Inventors: Alan Edward Rowan, Nijmegen (NL); Zaskia Hillet Eksteen Akeroyd, Nijmegen (NL); Christopher Wilson, S Yorks (GB); Petrus Johannes Geutjes, Nijmegen (NL); Wouter F. J. Feitz, Nijmegen (NL); Egbert Oosterwijk, Nijmegen (NL)

(73) Assignee: STICHTING KATHOLIEKE UNIVERSITEIT, Nijmegen (NL)

( * ) Notice: Subject to any disclaimer, the term of this patent is extended or adjusted under 35 U.S.C. 154(b) by 367 days.

(21) Appl. No.: 14/905,579

(22) PCT Filed: Jul. 16, 2014

(86) PCT No.: PCT/EP2014/065233
§ 371 (c)(1),
(2) Date: Jan. 15, 2016

(87) PCT Pub. No.: WO2015/007771
PCT Pub. Date: Jan. 22, 2015

(65) Prior Publication Data
US 2016/0137977 A1 May 19, 2016

(30) Foreign Application Priority Data

Jul. 18, 2013 (EP) .................................. 13003621

(51) Int. Cl.
C12N 5/071 (2010.01)
C08G 65/325 (2006.01)
C08G 65/333 (2006.01)
C08G 69/10 (2006.01)
C08G 69/40 (2006.01)
C07K 5/062 (2006.01)

(52) U.S. Cl.
CPC .......... C12N 5/069 (2013.01); C07K 5/06026 (2013.01); C08G 65/325 (2013.01); C08G 65/33324 (2013.01); C08G 69/10 (2013.01); C08G 69/40 (2013.01); C12N 5/0691 (2013.01); C12N 2502/28 (2013.01); C12N 2533/50 (2013.01)

(58) Field of Classification Search
CPC .. C08G 69/40; C08G 65/33324; C08G 69/48; C07K 5/06026; A61K 47/60
See application file for complete search history.

(56) References Cited

U.S. PATENT DOCUMENTS

2010/0215731 A1    8/2010  Emans et al.
2013/0202548 A1*   8/2013  Rowan ............. A61K 47/48192
                                                   424/78.17

FOREIGN PATENT DOCUMENTS

EP    2404618 A1    11/2012
GB    1103681       2/1968
WO    2010064251 A1    6/2010
WO    2011007012 A1    1/2011
WO    2011136645 A1    11/2011
WO    WO-2012004369 A1 *  1/2012  ....... A61K 47/48192
WO    2012158235 A2    11/2012

OTHER PUBLICATIONS

R. Ian Freshney, Culture of Animal Cells, A Manual of Basic Technique, Book, 2000, pp. 89-120, Fourth Edition, Wiley-Liss, Inc., published in the United States and Canada simultaneously.
Suginome, et al.,Transition Metal-Mediated Polymerization of Isocyanides, Advances in Polymer Science, 2004, pp. 77-136, , vol. 171, Springer Berlin Heidelberg, Japan.
Roeland J.M. Nolte, Helical Poly(isocyanides), Chemical Society Reviews, Jan. 1, 1994, pp. 11-19, vol. 23, Royal Society of Chemistry.
Michael B. Smith, et al., March's Advanced Organic Chemistry: Reactions, Mechanisms, and Structure, 2007, pp. 1-2374, John Wiley & Sons, Inc., Hoboken, New Jersey, published simultaneously in Canada.
Alan Doyle, et al., Cell and Tissue Culture: Laboratory Procedures in Biotechnology, 1998, pp. 1-354, John Wiley & Sons Ltd., England.
Matthieu Koepf, et al., Preparation and characterization of non-linear poly(ethylene glycol) analogs from oligo (ethylene glycol) functionalized polyisocyanopeptides, European Polymer Journal, 2013, pp. 1510-1522, vol. 49, Elsevier Ltd., The Netherlands.
Kouwer, et al., Responsive biomimetic networks from polyisocyanopeptide hydrogels, Nature, Jan. 31, 2013, pp. 651-655, vol. 493, Macmillan Publishers Limited.

* cited by examiner

Primary Examiner — Rachael E Bredefeld
Assistant Examiner — Kaipeen E Yang
(74) Attorney, Agent, or Firm — Hudak, Shunk & Farine Co. LPA (57) ABSTRACT A process for making an oligo(alkylene glycol) functionalized co-polyisocyanopeptide, wherein the process includes the steps of: i) copolymerizing a first comonomer of an oligo(alkylene glycol) functionalized isocyanopeptide grafted with a linking group and a second comonomer of a non-grafted oligo(alkylene glycol) functionalized isocyanopeptide, wherein the molar ratio between the first comonomer and the second comonomer is 1:500 and 1:30 and ii) adding a reactant of a spacer unit and a cell adhesion factor to the copolymer obtained by step i), wherein the spacer unit is represented by general formula A-L-B, wherein the linking group and group A are chosen to react and form a first coupling and the cell adhesion factor and group B are chosen to react and form a second coupling, wherein the first coupling and the second coupling are independently selected from the group consisting of alkyne-azide coupling, dibenzocyclooctyne-azide coupling, oxanorbornmadiene-based-azide couplings, vinylsulphone-thiol coupling, maleimide-thiol coupling, methyl methacrylate-thiol coupling, ether coupling, thioether coupling, biotin-strepavidin coupling, amine-carboxylic acid resulting in amides linkages, alcohol-carboxylic acid coupling resulting in esters linkages and NHS-Ester (N-Hydroxysuccinimide ester)-amine coupling and wherein group L is a linear chain segment having 10-60 bonds between atoms selected from C, N, O and S in the main chain.

12 Claims, 3 Drawing Sheets

POLYMER SUITABLE FOR USE IN CELL CULTURE

FIELD OF THE INVENTION

The present invention relates to a process for preparing a polymer suitable for use in a cell culture. The invention further relates to a use of the cell culture for making a prevascular system.

BACKGROUND OF THE INVENTION

Until now cell culture gel materials may be isolated from natural sources or completely synthetic. Gels such as collagen, which produce inherently lamellar structures, are incapable of forming complex 3D networks in isolation. Gels such as those derived from EHS mouse sarcoma cells resemble the extra cellular environment found in tissues much better than pure collagen and also provide three dimensional environment within which cells may grow and assemble in to complex architectures. Naturally derived gelators are difficult to fully characterise and require intensive batch to batch analysis to achieve this characterisation, biologically derived gels suffer from inherent variability, risk of contamination and pathogen transfer along with excessive price premiums. For many research groups, additional trace contamination such as unwanted growth factors inherently present in biologically sourced materials are unacceptable experimental interferences and are unacceptable for use in-vivo. At the other end of the spectrum, synthetically derived gels such as those derived from poly (N-isopropylacrylamide) co-polymers exhibit low cell viability and cell differentiation ability, which requires additional mixtures of bioactives such as glucocorticoids and transforming growth factor beta (TGF-β). The use of synthetic gelators largely removes the natural variation found in biological gelators, but concomitantly eliminates the inherent biological activity of natural gels. The ability to eliminate the biological variability whilst retaining biological activity is a challenge not yet fully realised.

The ability to harvest complex biological systems formed in these gels also remains a challenge. Traditionally cells must be released from biological surfaces by the use of tripsin or for the gel to be mechanically dissolved or manually removed from the surface of the structure.

Gelatable structures demonstrated above are not universal in nature and cannot be easily applied in a minimally invasive way in-vivo. Some examples of themoresponsive materials that can be applied in a minimally invasive manner through a cooled catheter exist, such as those disclosed in US 2010/0215731 A1. However these materials suffer from the same drawbacks as described above resulting in poor cell viability.

Mechanically the properties of all of the biologically derived gels are dictated by the non-covalent interactions of the peptide subunits. The result is that the pore size and mechanical strength are relatively fixed. The mechanical properties and nature of the cross links are even more so fixed in the case of the synthetically derived gels.

WO 2011/007012 discloses a hydrogel comprising oligo (alkylene glycol) functionalized polyisocyanopeptides. The polyisocyanopeptides are prepared by functionalizing an isocyanopeptide with oligo-(alkylene glycol) side chains and subsequently polymerizing the oligo-alkylene glycol functionalized isocyanopeptides. WO2011/007012 suggests use of the hydrogels for tissue engineering or neuron regeneration.

Although the known cell cultures are satisfactory for some applications, there is an increased need in the art for cell cultures which can be used in a wide range of situations.

SUMMARY OF THE INVENTION

An objective of the present invention is to provide a cell culture and a polymer for use in the cell culture, where the above-mentioned and/or other needs in the art are met.

According to one aspect, the present invention provides a process for making an oligo(alkylene glycol) functionalized co-polyisocyanopeptide, wherein the process comprises the steps of: i) copolymerizing a first comonomer of an oligo (alkylene glycol) functionalized isocyanopeptide grafted with a linking group and a second comonomer of a non-grafted oligo(alkylene glycol) functionalized isocyanopeptide, wherein the molar ratio between the first comonomer and the second comonomer is 1:500 and 1:30 and ii) adding a reactant of a spacer unit and a cell adhesion factor to the copolymer obtained by step i), wherein the spacer unit is represented by general formula A-L-B, wherein the linking group and group A are chosen to react and form a first coupling and the cell adhesion factor and group B are chosen to react and form a second coupling, wherein the first coupling and the second coupling are independently selected from the group consisting of alkyne-azide coupling, dibenzocyclooctyne-azide coupling, oxanorbornadiene-based-azide couplings, vinylsulphone-thiol coupling, maleimide-thiol coupling, methyl methacrylate-thiol coupling, ether coupling, thioether coupling, biotin-strepavidin coupling, amine-carboxylic acid resulting in amides linkages, alcohol-carboxylic acid coupling resulting in esters linkages and NHS-Ester (N-Hydroxysuccinimide ester)-amine coupling and wherein group L is a linear chain segment having 10-60 bonds between atoms selected from C, N, O and S in the main chain.

The linking group and group A are chosen to react and form a first coupling which may be any coupling mentioned in the above list. For example, in order to obtain an alkyne-azide coupling, the linking group may be alkyne and group A may be azide or the linking group may be azide and group A may be alkyne. The couplings mentioned in the above list are well-known to the skilled person and the formation of the couplings are found in textbooks. For example, $NH_2$—COOH coupling can be mediated via EDC.

Preferably, the first coupling is an alkyne-azide coupling.

Similarly, the cell adhesion factor and group B are chosen to react and form a second coupling which may be any coupling mentioned in the above list. Preferably, the second coupling is NHS-Ester (N-Hydroxysuccinimide ester)-amine coupling or maleimide-thiol coupling. This may be a coupling of NHS-ester to the N terminus of a the cell adhesion factor being a peptide or a coupling of maleimide to a terminal thiol of the cell adhesion factor being a peptide.

Group L is a segment having a linear chain connecting reactive groups A and B. The segment is formed by a sequence of atoms selected from C, N, O and S. The number of bonds between the atoms in the main chain connected to groups A and B is at least 10 and at most 60. The term 'main chain' is understood to mean the chain which connects the groups A and B with the shortest distance. The number of bonds between the atoms in the main chain connected to the terminal groups A and B is preferably at least 12, more preferably at least 15. The number of bonds between the atoms in the main chain connected to the terminal groups A and B is preferably at least 50, more preferably at least 40.

It was found that a certain minimum distance between the copolymer backbone and the cell adhesion factor is required for the cells attached to the cell adhesion factor to be cultured. The distance given by at least 10 bonds was found to be necessary, which is provided by the presence of the spacer unit according to the invention. The length below 10 bonds was found not to allow sufficient cell growth.

Preferred examples of group L are the following:

where p is 1 to 10, preferably 2 to 5, where q is 1 to 9, preferably 2 to 5.

where r is 1 to 10, preferably 2 to 5.

When the spacer unit contains these types of group L, particularly stable cell growth is ensured independent on the type and size of groups A and B, the linking group and the cell adhesion factor.

According to a further aspect, the present invention provides the oligo(alkylene glycol) functionalized co-polyisocyanopeptide obtainable by the process according to the present invention.

According to a further aspect, the present invention provides a cell culture comprising a hydrogel comprising an oligo(alkylene glycol) functionalized co-polyisocyanopeptide at a concentration of 1.2-3.0 mg/mL, wherein the co-polyisocyanopeptide is made by: i) copolymerizing a first comonomer of an oligo(alkylene glycol) functionalized isocyanopeptide grafted with a linking group and a second comonomer of a non-grafted oligo(alkylene glycol) functionalized isocyanopeptide, wherein the molar ratio between the first comonomer and the second comonomer is 1:500 and 1:30 and ii) adding a reactant of a spacer unit and a cell adhesion factor to the copolymer obtained by step i), wherein the spacer unit is represented by general formula A-L-B, wherein the linking group and group A are chosen to react and form a first coupling and the cell adhesion factor and group B are chosen to react and form a second coupling, wherein the first coupling and the second coupling are independently selected from the group consisting of alkyne-azide coupling, dibenzocyclooctyne-azide coupling, oxanorbornadiene-based-azide couplings, vinylsulphone-thiol coupling, maleimide-thiol coupling, methyl methacrylate-thiol coupling, ether coupling, thioether coupling, biotin-strepavidin coupling, amine-carboxylic acid resulting in amides linkages, alcohol-carboxylic acid coupling resulting in esters linkages and NHS-Ester (N-Hydroxysuccinimide ester)-amine coupling and wherein group L is a linear chain segment having 10-60 bonds between atoms selected from C, N, O and S in the main chain.

The inventors have surprisingly found that an optimal cell growth is achieved only under specific concentrations of the cell adhesion factors which are positioned at a certain distance from the polymer backbone which constructs the three-dimensional structure of the hydrogel.

If the concentration of the cell adhesion factor is too low, the cells do not adhere sufficiently to the hydrogel which in turn does not allow the cells to be cultured. If the concentration of the cell adhesion factor is too high, the cells do not grow in the gel.

The first comonomer is an oligo(alkylene glycol) functionalized isocyanopeptide grafted with a linking group. Preferred examples of the linking group include azide (e.g oxanorbomadiene-based-azide), alkyne (e.g. dibenzocyclooctyne), thiol, vinylsulphone, maleimide, methyl methacrylate, ether, biotin, strepavidin, $NH_2$, COOH, OH, NHS-ester. Particularly preferred is azide.

An example of the first comonomer is shown in Formula (I), in which the linking group is an azide.

The second comonomer is an oligo(alkylene glycol) functionalized isocyanopeptide which is not grafted with a linking group or other groups, i.e. the side chain of the isocyanopeptide consists of an oligo(alkylene glycol). An example of the second comonomer is shown in Formula (II).

The first comonomer and the second comonomer are copolymerized in step (i). An oligo(alkylene glycol) functionalized co-polyisocyanopeptide is obtained comprising linking groups along the polymer in the ratio of the first comonomer and the second comonomer.

A cell adhesion factor is attached to the copolymer via a spacer unit. First, a reactant of a spacer unit and a cell adhesion factor is made. An example of the spacer unit is shown in Formula (III).

where p is 1 to 10.

In this example, group A is group B is group L is

An example of the cell adhesion factor is shown in Formula (IV), which is a pentapeptide composed of glycine, L-arginine, glycine, L-aspartic acid, and serine (GRGDS).

(IV)

The reactant of the spacer unit of (III) and the cell adhesion factor of (IV) is shown in Formula (V).

(V)

In step ii) of the invention, the reactant (e.g. formula (V)) of a spacer unit and a cell adhesion factor is reacted with the copolymer obtained by step i). The linking group reacts with the part of the reactant corresponding to the spacer unit. Accordingly, the final co-polyisocyanopeptide comprises cell adhesion units along the polymer in the ratio of the first comonomer and the second comonomer. An example of the final co-polyisocyanopeptide is represented by Formula (VI):

(VI)

where m:n is the ratio of the first comonomer to the second comonomer.

The cell adhesion unit is positioned at a distance from the isocyanopeptide polymer backbone by the use of the spacer unit.

A hydrogel is made from the copolymer as obtained by gelling with a suitable cell culture medium. The hydrogel is a three dimensional hydrogel. The polymer concentration in the hydrogel is 1.2-3.0 mg/mL. If the polymer concentration in the hydrogel is too low, cells do not adhere to the hydrogel. If the polymer concentration in the hydrogel is too high, the hydrogel becomes too stiff for the cells to move and grow within the gel.

Preferably, the hydrogel has an elastic modulus in the range 10-5000 Pa, preferably 100-1000 Pa at 35° C. as determined by plate-plate rheology experiments. This allows the cells to move and grow to form cellular network and 3D structures, like for example a prevascular system.

The present invention provides a cell culture of a hydrogel having a selective stiffness and temperature responsiveness as well as controlled spacial distribution and density of cell adhesion points. The co-polymerisation results in a statistical distribution of the cell adhesion group along the copolymer in the ratio of the first comonomer and the second comonomer. The ratio between the first comonomer and the second comonomer can be tuned to control the distance between the cell adhesion factors along the polymer backbone of polyisocyanopeptide. The average distance between the cell adhesion factors along the polymer backbone may e.g. be 1.1-60 nm. This range of the distance between the cell adhesion factors is suitable for anchoring the cells to be cultured to the cell culture. More preferably, the average distance between the cell adhesion factors is 8-30 nm.

The hydrogel may comprise a variety of cell culture media and the cell culture has been shown to mediate the formation of complex biological scaffold.

The cell culture according to the invention is extremely advantageous in that the collection of the cultured cells is easy. The hydrogel used in the cell culture has a thermo-responsive character, i.e. it turns to liquid by cooling it to a temperature below the gelling temperature. Hence the collection of the cultured cells can be performed by only cooling the cell culture. After the hydrogel turns to liquid, the cells can be collected from the liquid without damaging the cultured cells.

It was determined that the cell adhesion factor cannot be directly attached to the oligo-alkylene glycol functionalized isocyanopeptides to retain sufficient binding. This was solved by the use of a spacer according to the present invention. The spacer unit used according to the invention separates the cell adhesion factor from the polymer backbone of isocyanopeptides to eliminate steric blocking. The spacer decouples the motions of the cell adhesion factor from the polymer backbone and decoupling the motions allows the cell adhesion factor to dock efficiently into the integrin binding pocket. The spacer should be polar, water soluble, biocompatible and non-binding to the active site of the integrin, but can aid in auxiliary binding. The first monomer may be made by first preparing a second monomer and grafting it with a linking group. Alternatively, the first monomer and the second monomer may be made through different routes.

The molar ratio between the first comonomer and the second comonomer is between 1:500 and 1:30. Preferably, the molar ratio between the first comonomer and the second comonomer is between 1:400-1:35, 1:300-1:40 or 1:200-1:45. This range of the ratio between the first comonomer and the second comonomer gives an average distance of 8-30 nm between the cell adhesion units along the polymer backbone.

Preferably, the oligo(alkylene glycol) functionalized co-polyisocyanopeptide has a gelation temperature of 18-40° C. The gelation temperature is independent of the polymer concentration in the hydrogel. Rather it is dependent on the number of oligoalkylene glycol units in the side chain of the polymer.

Further details of the present invention are given below.

Comonomers

Functionalizing isocyanopeptide with oligo(alkylene glycol) Units.

The monomers are preferably based on a di-, tri-, tetra- or more peptidic motif substituted at the C terminal with the desired oligo(alkylene glycol) chains. The chains may be based on linear, branched or dendronized oligo(alkylene oxide).

Preferably the chain is linear and is composed of ethylene glycol.

The peptidic segment can be of different compositions determined by the sequence of natural or non-natural and expanded amino-acids or mixture thereof.

The monomers are derived from adequate oligo(alkylene glycol) fragments. A multi-steps peptidic coupling strategy is used to introduce successively the desired amino-acids. Following the introduction of the desired peptidic sequence, the N-terminus of the peptidic segment is formylated with an adequate formylation method. This formylation may include the treatment of the product with formyl salts, formic acid, or other formylating agents.

Some examples of formylation strategies make use of formate salts (such as sodium or potassium formate), alkyl formates (such as methyl-, ethyl-, or propyl-formate), formic acid, chloral and derivatives. The isocyanide is then formed by treating the formamide with an appropriate dehydration agent. An example of dehydratation strategy uses diphogene. Several examples of dehydratation agents that may also be used are phosgene and derivatives (di-, triphosgene), carbodiimides, tosyl chloride, phosphorous oxachloride, triphenylphosphine/tetrachlorocarbon, [M. B. Smith and J. March "March's advanced organic chemistry" 5th edition, Wiley & Son eds., 2001, New York, USA, pp 1350-1351 and ref. herein;]

Side chains (alkylene glycol)

Examples of suitable alkylene glycols are ethylene-, propylene-, butylene- or pentylene glycol. Preferably the alkylene glycol is ethylene glycol.

Advantageous oligoethyleneglycol units are depicted below. In general, the term oligo refers to a number <10.

1 OEG

2 OEG

Preferably the isocyanopeptides are functionalized with at least 3 ethylene glycol units to lead to water soluble materials after polymerization.

The second comonomer of the present invention is an oligo(alkylene glycol)isocyanopeptide as described above, without further grafting.

The first comonomer may consist of an isocyanopeptide having the same number of alkylene glycol units or may be a mixture of isocyanopeptides having different number of alkylene glycol units. Similarly, the second comonomer may consist of an isocyanopeptide having the same number of alkylene glycol units or may be a mixture of isocyanopeptides having different number of alkylene glycol units.

The first comonomer and the second comonomer are oligo(alkylene glycol) functionalized isocyanopeptide, i.e. the number of the alkylene glycol units on the isocyanopeptide is 1 to 10. Preferably, the average of the number of the alkylene glycol units on the first comonomer and the second comonomer is at least 3 and at most 4.

The average of the alkylene glycol units on the first comonomer and the second comonomer is typically tuned by using a mixture of isocyanopeptides having different numbers of alkylene glycol units as the second comonomer. In preferred embodiments, the first comonomer is an isocyanopeptide having three alkylene glycol units and the second comonomer is a mixture of an isocyanopeptide having three alkylene glycol units and an isocyanopeptide having four alkylene glycol units.

The average of the number of the alkylene glycol units on the first comonomer and the second comonomer may be 3. The gelation temperature of 15-25° C. is typically obtained. The average of the number of the alkylene glycol units on the first comonomer and the second comonomer may be more than 3 and at most 3.5. The gelation temperature of 18-35° C. is typically obtained. The average of the number of the alkylene glycol units on the first comonomer and the second comonomer may be more than 3.5 and at most 5. The gelation temperature of 25-50° C. is typically obtained.

Preferably, the oligo(alkylene glycol) functionalized copolyisocyanopeptide has an elastic modulus of 10-5000 Pa, preferably 100-1000 Pa at a temperature of 35° C. as determined by rheology measurements. When the average of the number of the alkylene glycol units on the first comonomer and the second comonomer is at least 3 and at most 5, the hydrogel has such stiffness.

Polymerization

The oligo(alkylene glycol)isocyanopeptide monomer grafted with the linking group (first comonomer) and the oligo(alkylene glycol)isocyanopeptide monomers not grafted with the linking group (second comonomer) are mixed and subsequently copolymerized.

The copolymerization is preferably performed in the presence of an apolar solvent. Suitable apolar solvents may be selected from the group consisting of saturated hydrocarbon solvents and aromatic hydrocarbon solvents or mixtures thereof. Examples of apolar solvents are pentane, hexane, heptane, 2-methylbutane, 2-methylhexane, cyclohexane, and toluene, benzene xylenes or mixtures thereof. Preferably toluene is used in the polymerization. Preferably toluene is chosen for the polymerization process of oligo (ethylene glycol)isocyanopeptides where the oligo(ethylene glycol) part contains at least three ethylene glycol units.

Preferably the polymerization is carried out in the presence of a catalyst. The catalyst is preferably a nickel(II) salt. Example of Ni(II) salts are nickel(II) halides (e.g. nickel(II) chloride), nickel(II) perchlorate or tetrakis-(tertbutylisocyanide)nickel(II) perchlorate.

Other complexes and nickel salts might be used provided that they are soluble in the polymerization medium or initially dissolved in an adequate solvent which is miscible in the polymerization medium. General references describing some catalytic systems that may be used to polymerize the oligo(alkylene glycol)isocyanopeptides may be found in Suginome M.; Ito Y; Adv Polym SC1 2004, 171, 77-136; Nolte R. J. M.; Chem. Soc. Rev. 1994, 23(1), 11-19)]

Preferably the monomer concentration is chosen above 30 mmol/L and the catalyst/monomer ratio chosen between 1/100 and 1/10 000. Lowering the amount of nickel(II) (catalyst/monomer ratio below 1/1000) permits the preparation of materials exhibiting a substantial degree of polymerization [mean DP>500], which is desired for subsequent application of the polymers as macro-hydrogelators.

In a representative example, a millimolar solution of monomer in a nonpolar organic solvent or mixture of solvents is added to a nickel (II) catalyst dissolved in a polar solvent in a molar ratio of 1:50 up to 1:100,000 catalyst to monomer. In a sealed environment the mixture is vigorously stirred for 2 to 24 hrs. Once completed, the reaction mixture is evaporated and the crude product is dissolved in organic solvents and precipitated in diethylether or similar noncompatible organic solvents, giving the desired product.

Grafting of Reactant of Spacer Unit and Cell Adhesion Factor to Linking Group

Spacer Unit

The terminal groups A and B are preferably chosen such that the synthesis of the subsequent compound is possible without the need for deprotection or activation steps.

Preferred examples of group A of the spacer unit include azide (e.g oxanorbornadiene-based-azid), alkyne (e.g. dibenzocyclooctyne), thiol, vinylsulphone, maleimide, methyl methacrylate, ether, biotin, strepavidin, $NH_2$, COOH, OH, NHS-ester. Particularly preferred is alkyne.

Preferred examples of group B of the spacer unit include azide (e.g oxanorbornadiene-based-azid), alkyne (e.g. dibenzocyclooctyne), thiol, vinylsulphone, maleimide, methyl methacrylate, ether, biotin, strepavidin, NH₂, COOH, OH, NHS-ester. Particularly preferred is NHS-ester or malemide.

Preferably, the group A of the spacer unit is represented by formula (VII):

(VII)

wherein:

n is 0 to 8;

R³ is selected from the group consisting of [(L)$_p$-Q], hydrogen, halogen, C$_1$-C$_{24}$ alkyl groups, C$_6$-C$_{24}$ (hetero)aryl groups, C$_7$-C$_{24}$ alkyl(hetero)aryl groups and C$_7$-C$_{24}$ (hetero)arylalkyl groups, the alkyl groups optionally being interrupted by one of more hetero-atoms selected from the group consisting of O, N and S, wherein the alkyl groups, (hetero)aryl groups, alkyl(hetero)aryl groups and (hetero)arylalkyl groups are independently optionally substituted with one or more substituents independently selected from the group consisting of C$_1$-C$_{12}$ alkyl groups, C$_2$-C$_{12}$ alkenyl groups, C$_2$-C$_{12}$ alkynyl groups, C$_3$-C$_{12}$ cycloalkyl groups, C$_1$-C$_{12}$ alkoxy groups, C$_2$-C$_{12}$ alkenyloxy groups, C$_2$-C$_{12}$ alkynyloxy groups, C$_3$-C$_{12}$ cycloalkyloxy groups, halogens, amino groups, oxo groups and silyl groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S, wherein the silyl groups are represented by the formula (R⁴)₃Si—, wherein R⁴ is independently selected from the group consisting of C$_1$-C$_{12}$ alkyl groups, C$_2$-C$_{12}$ alkenyl groups, C$_2$-C$_{12}$ alkynyl groups, C$_3$-C$_{12}$ cycloalkyl groups, C$_1$-C$_{12}$ alkoxy groups, C$_2$-C$_{12}$ alkenyloxy groups, C$_2$-C$_{12}$ alkynyloxy groups and C$_3$-C$_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S;

R¹ is independently selected from the group consisting of hydrogen, C$_1$-C$_{24}$ alkyl groups, C$_6$-C$_{24}$ (hetero)aryl groups, C$_7$-C$_{24}$ alkyl(hetero)aryl groups and C$_7$-C$_{24}$ (hetero)arylalkyl groups; and

R² is independently selected from the group consisting of halogen, —OR⁶, —NO₂, —CN, —S(O)₂R⁶, C$_1$-C$_{12}$ alkyl groups, C$_1$-C$_{12}$ aryl groups, C$_1$-C$_{12}$ alkylaryl groups and C$_1$-C$_{12}$ arylalkyl groups, wherein R⁶ is as defined above, and wherein the alkyl groups, aryl groups, alkylaryl groups and arylalkyl groups are optionally substituted.

Preferably, n=0.

Preferably, R1 is hydrogen.

Preferably, R3 is hydrogen.

Preferably, the group B of the spacer unit is represented by formula (VIII):

(VIII)

Preferably, the spacer unit comprises the group A of formula (VII) and the group B of formula (VIII).

Examples of the suitable spacer unit include the compounds represented by formula (IX):

(IX)

wherein R1, R2, R3 and n are as defined above and

L is preferably selected from the group represented by formula (X-1), (X-2, (X-3):

(X-1)

where p is 1 to 10, preferably 2 to 5, (X-2)

where q is 1 to 9 preferably 2 to 5.

(X-3)

where r is 1 to 10, preferably 2 to 5

Preferably, the spacer unit is represented by Formula (XI).

wherein p is 1 to 10, preferably 2 to 5, more preferably 2.

Other examples of the suitable spacer unit include fused cyclooctyne compounds described in WO2011/136645, which is incorporated herein by reference. Accordingly, a possible spacer unit is selected from the compound of the Formula (IIa, (IIb) or (IIc):

wherein:
n is 0 to 8;
p is 0 or 1;
$R^3$ is selected from the group consisting of $[(L)_p\text{-}Q]$, hydrogen, halogen, $C_1\text{-}C_{24}$ alkyl groups, $C_6\text{-}C_{24}$ (hetero)aryl groups, $C_7\text{-}C_{24}$ alkyl(hetero)aryl groups and $C_7\text{-}C_{24}$ (hetero)arylalkyl groups, the alkyl groups optionally being interrupted by one or more hetero-atoms selected from the group consisting of O, N and S, wherein the alkyl groups, (hetero)aryl groups, alkyl(hetero)aryl groups and (hetero)arylalkyl groups are independently optionally substituted with one or more substituents independently selected from the group consisting of $C_1\text{-}C_{12}$ alkyl groups, $C_2\text{-}C_{12}$ alkenyl groups, $C_2\text{-}C_{12}$ alkynyl groups, $C_3\text{-}C_{12}$ cycloalkyl groups, $C_1\text{-}C_{12}$ alkoxy groups, $C_2\text{-}C_{12}$ alkenyloxy groups, $C_2\text{-}C_{12}$ alkynyloxy groups, $C_3\text{-}C_{12}$ cycloalkyloxy groups, halogens, amino groups, oxo groups and silyl groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S, wherein the silyl groups are represented by the formula $(R^4)_3Si{-}$, wherein $R^4$ is independently selected from the group consisting of $C_1\text{-}C_{12}$ alkyl groups, $C_2\text{-}C_{12}$ alkenyl groups, $C_2\text{-}C_{12}$ alkynyl groups, $C_3\text{-}C_{12}$ cycloalkyl groups, $C_1\text{-}C_{12}$ alkoxy groups, $C_2\text{-}C_{12}$ alkenyloxy groups, $C_2\text{-}C_{12}$ alkynyloxy groups and $C_3\text{-}C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N and S;

L is a linking group selected from linear or branched $C_1\text{-}C_{24}$ alkylene groups, $C_2\text{-}C_{24}$ alkenylene groups, $C_2\text{-}C_{24}$ alkynylene groups, $C_3\text{-}C_{24}$ cycloalkylene groups, $C_5\text{-}C_{24}$ cycloalkenylene groups, $C_8\text{-}C_{24}$ cycloalkynylene groups, $C_7\text{-}C_{24}$ alkyl(hetero)arylene groups, $C_7\text{-}C_{24}$ (hetero)arylalkylene groups, $C_8\text{-}C_{24}$ (hetero)arylalkenylene groups, $C_9\text{-}C_{24}$ (hetero)arylalkynylene groups, the alkylene groups, alkenylene groups, alkynylene groups, cycloalkylene groups, cycloalkenylene groups, cycloalkynylene groups, alkyl(hetero)arylene groups, (hetero)arylalkylene groups, (hetero)arylalkenylene groups and (hetero)arylalkynylene groups optionally being substituted with one or more substituents independently selected from the group consisting of $C_1\text{-}C_{12}$ alkyl groups, $C_2\text{-}C_{12}$ alkenyl groups, $C_2\text{-}C_{12}$ alkynyl groups, $C_3\text{-}C_{12}$ cycloalkyl groups, $C_5\text{-}C_{12}$ cycloalkenyl groups, $C_8\text{-}C_{12}$ cycloalkynyl groups, $C_1\text{-}C_{12}$ alkoxy groups, $C_2\text{-}C_{12}$ alkenyloxy groups, $C_2\text{-}C_{12}$ alkynyloxy groups, $C_3\text{-}C_{12}$ cycloalkyloxy groups, halogens, amino groups, oxo and silyl groups, wherein the silyl groups can be represented by the formula $(R^4)_3Si{-}$, wherein $R^4$ is defined as above;

Q is a functional group selected from the group consisting of hydrogen, halogen, $R^6$, $-CH{=}C(R^6)_2$, $-C{\equiv}CR^6$, $-[C(R^6)_2C(R^6)_2O]_q{-}R^6$, wherein q is in the range of 1 to 200, $-CN$, $-N_3$, $-NCX$, $-XCN$, $-XR^6$, $-N(R^6)_2$, $-{}^+N(R^6)_3$, $-C(X)N(R^6)_2$, $-C(R^6)_2XR^6$, $-C(X)R^6$, $-C(X)XR^6$, $-S(O)R^6$, $-S(O)2R^6$, $-S(O)OR^6$, $-S(O)_2OR^6$, $-S(O)N(R^6)_2$, $-S(O)_2N(R^6)_2$, $-OS(O)R^6$, $-OS(O)_2R^6$, $-OS(O)OR^6$, $-OS(O)_2OR^6$, $-P(O)(R^6)(OR^6)$, $-P(O)(OR^6)_2$, $-OP(O)(OR^6)_2$, $-Si(R^6)_3$, $-XC(X)R^6$, $-XC(X)XR^6$, $-XC(X)N(R^6)_2$, $-N(R^6)C(X)R^6$, $-N(R^6)C(X)XR^6$ and $-N(R^6)C(X)N(R^6)_2$, wherein X is oxygen or sulphur and wherein $R^6$ is independently selected from the group consisting of hydrogen, halogen, $C_1$-$C_{24}$ alkyl groups, $C_6$-$C_{24}$ (hetero) aryl groups, $C_7$-$C_{24}$ alkyl(hetero)aryl groups and $C_7$-$C_{24}$ (hetero)arylalkyl groups;

$R^1$ is independently selected from the group consisting of hydrogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups; and $R^2$ is independently selected from the group consisting of halogen, —$OR^6$, —$NO_2$, —$CN$, —$S(O)_2R^6$, $C_1$-$C_{12}$ alkyl groups, $C_1$-$C_{12}$ aryl groups, $C_1$-$C_{12}$ alkylaryl groups and $C_1$-$C_{12}$ arylalkyl groups, wherein $R^6$ is as defined above, and wherein the alkyl groups, aryl groups, alkylaryl groups and arylalkyl groups are optionally substituted.

Cell Adhesion Factor

The cell adhesion factor supports the binding of cells to the gel. The cell adhesion factor preferably is a sequence of amino acids. Examples of amino acids that advantageously may be used in the present invention are N-protected Alanine, Arginine, Asparagines, Aspartic acid, Cysteine, Glutamic acid, Glutamine, Glycine, Histidine, Isoleucine, Leucine, Lysine, Methionine, Phenylalanine, Proline, Serine, Threonine, Thryptophan, Tyrosine, Valine. Suitable sequences of amino acids include peptides such as RGD, GRGDS, IKVAV, KQAGDV and GRGDSP. The cell adhesion factor may also be a growth factor such as VGEF and BFGF. The cell adhesion factor may also be glycoproteins or mucins.

The spacer unit and the cell adhesion factor are reacted. The reactant may be grafted to the linking group of the copolymer by copper free SPAAC reaction.

General Properties of the Polymer

Figure 1:
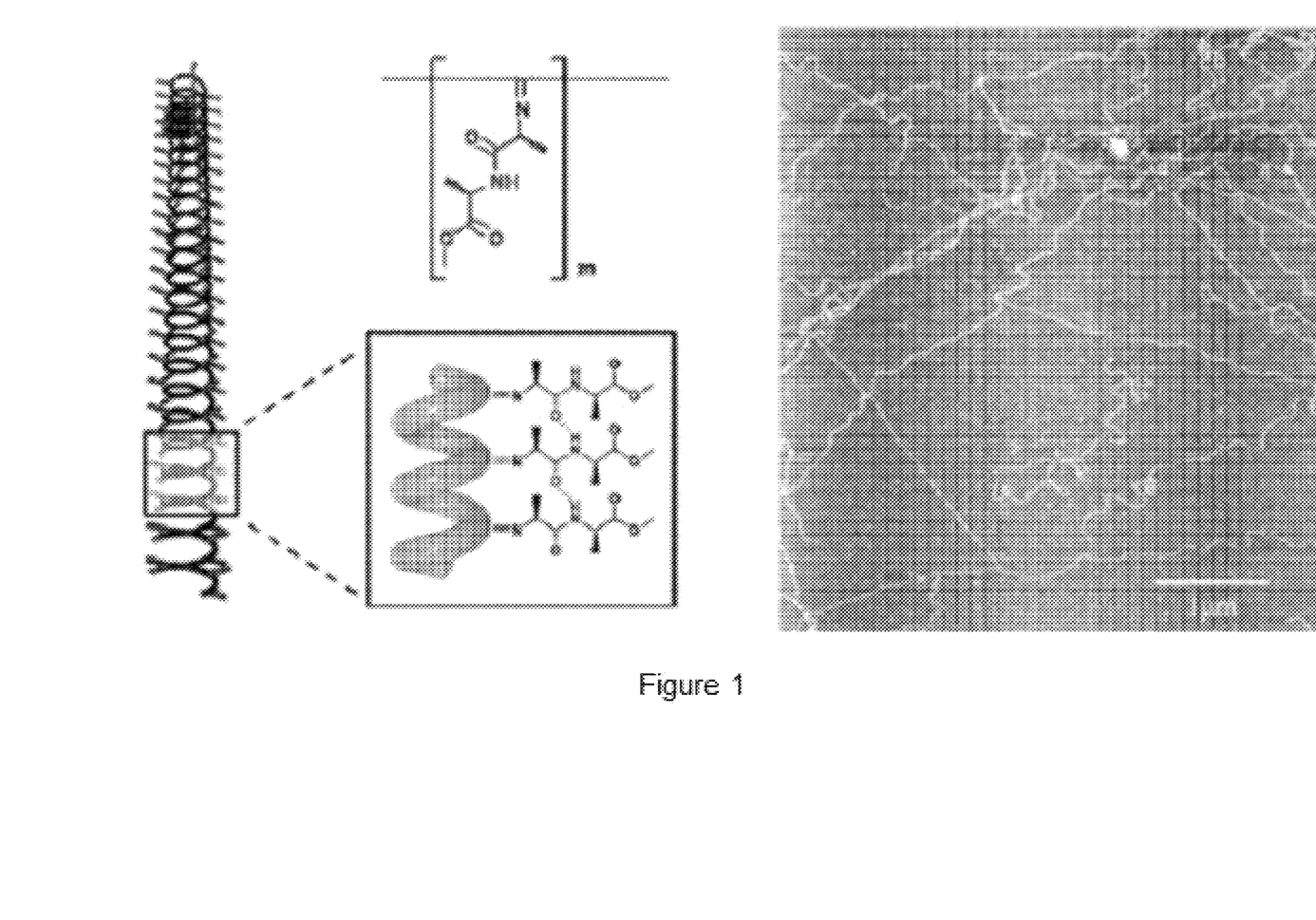
FIG. 1 illustrates a schematic representation of the helical oligo-alkylene functionalized polyisocyano-peptides based on a dialane unit (top middle). The backbone folding is stabilized by a hydrogen bounding network that develops within the helix, between the stacked amides bounds of the side chains (down-middle). This secondary structure leads to very stiff chains as visualized by AFM (right).

The polyisocyanopeptides used in the present invention exhibit a well defined structure, such as a perfect oligo (alkylene glycol) coated beta-sheet helical structure, according to FIG. 1. This structure comprises a helical poly(imine) core in which virtually each nitrogen is substituted with a peptidic pendant. Due to the pseudo $4_1$ helical symmetry of the poly(imine) backbone every pendants grafted onto the nth nitrogen is involved in an intramolecular beta-sheet like packing with the corresponding pendant grafted onto the n+4$^{th}$ position. The peptidic segments are further decorated with oligo(alkylene glycol) substituents that form the outer shell of the structure. The water solubility of the resulting materials is directly related to the choice of adequate oligo (ethylene glycol) substituents. Finally, the helical sense of the polymer chain is dictated by the chirality of amino-acids connected to the imine groups.

The polyisocyanopeptides used in the present invention has minimal or no structural defects in the polymers obtained. The term minimal is to be interpreted as that more than 96% of the correct side chains are correctly attached to the polymer backbone, such as 97%, 98%, 99%, 99.5% or even 100%.

In other words, due to the direct polymerization of functionalized monomers, occurrence of structural defects regarding the grafting density of the side chains is minimal in the resulting materials.

The polyisocyanopeptides used in the present invention can be homogeneous, stable, water soluble helical polymers of high degree of polymerization [DP]>500 and high persistence length.

The invention provides homogeneous hydrogels comprising the oligoalkylene functionalized polyisocyanopeptides and also heterogeneous hydrogels comprising mixtures oligoalkylene functionalized polyisocyanopeptides with differing number of ethylene glycol units.

The obtained oligoalkylene functionalized polyisocyanopeptides are capable to form strong thermoreversible hydrogels with tunable gelation temperature. To physically gel water, the poly[oligo(ethylene glycol)isocyanopeptides according to the invention preferably have a degree of polymerization [DP]>500.

A hydrogel is made from the copolymer as obtained by gelling with a suitable cell culture medium. The hydrogel is a three dimensional hydrogel. The polymer concentration in the hydrogel is 1.2-3.0 mg/mL. If the polymer concentration in the hydrogel is too low, the hydrogel is too weak to support the growth of the cellular 3D network. If the polymer concentration in the hydrogel is too high, the hydrogel becomes too stiff for the cells to move and grow within the gel.

Preferably, the hydrogel has an elastic modulus of 10-5000 Pa at 35° C. as determined by rheology experiments. This allows the cells to move and grow to form a 3D cell structure like for example a prevascular system.

The hydrogels obtained from the oligo(alkylene glycol) polyisocyanopeptides used in the invention differ from most of the previously reported polymer-based hydrogels in the highly structured nature of the network formed upon gelation. The network consists of twisted bundles of laterally aggregated polymer chains. This arrangement is similar to the structure of the fibrilar networks that are formed upon the gelation of low molecular weight hydrogelators. It is supposed that this phenomenon is related to the high persistence length of the polyisocyanopeptides that favor an original mode of association. The association is triggered by the temperature induced modulation of oligo(alkylene glycol) side chains hydrophilicity which is a perfectly reversible phenomenon, resulting in a completely thermorevesible aggregation/dissolution of the oligo(alkylene glycol) functionalized polyisocyanopeptides.

Classical description of physical polymer hydrogels comprises the formation of an entanglement network chains in concentrated solutions, formation of a percolation network due to spinodal demixing, micro-crystallites formation, and formation of micelles network or lamellar structures which seemingly differ from the postulated association mode of the oligo(alkylene glycol)polyisocyanopeptide.

The hydrogels resulting from the oligo(alkylene glycol) polyisocyanopeptide result from the lateral association of polymers fibers of about 5 nm in diameter into larger twisted bundles that form the base of the polymeric hydrogel network. This results in a highly porous structure with pore size that can go down to 50 nm in diameter.

Due to the thermosensitive behaviour of ethylene glycol side chains, the polymers used in the present invention present clear LCST transitions. For a given oligo(alkylene glycol)polyisocyanopeptide this temperature can be modified by varying the ionic strength of the solution (salt effect) or more generally by the addition of any compounds able to modify the overall solvation state of the polymers. The LCST of the materials can be further modulated by acting on the poly(isocyanide) backbone and namely on its conformation, with the use of acids or any compounds that can lead to conformational changes of the backbone helix.

Another way to modulate the LCST of the polymers is to co-polymerize monomers bearing different oligo(alkylene glycol) side chains. For example the polymerization of mixtures of tri- and tetra(ethylene glycol)isocyanodialanine in different ratio permitted to adjust the gellation temperature of the resulting copolymers between 22° C. and 60° C. in mQ water.

It has been found that the polymer chain length influences the gelation. The chains with lower degree of polymerization had a strong tendency to precipitate rather than to form gels. It is expected that this is a general effect for stiff or semi flexible polymers which hydrophilicity can be varied without modifying the general structure of the chains (i.e. in rigid structures the chain does not collapse but rather aggregates laterally with others chains to form extended fibers).

A further influence of polymers length has been observed in relation to the optical properties of the resulting gels. It was found that hydrogels prepared from chains with a lower degree of polymerization were prone to be turbid or opaque. Increasing the mean degree of polymerization resulted in a decrease of opacity of the hydrogels leading eventually to fully optically transparent materials.

The gel temperature may be adjusted to some extent, with the possibility to form stable structured gels at 25° C., leading therefore to a new biomimetic matrix which can be used to encapsulate enzymes or cells and preserve their activity in vitro.

The polymers used in the invention appeared to have some interesting and advantageous properties. Due to the length and the stiffness of the polymer, the gels in some cases were made up of 99.00 to 99.98% water. This means that there is only very little material required to generate a large volume. A single wire of the polymer appeared to have a diameter of approximately 4 nanometer and a molecular weight of 2,500,000 Da. The polydispersity index (PDI) was 1.6 and an average chain length varied between 500 nm-2 micrometer. The polymers appeared to be rather stiff, having a persistence length of 70-90 nm. It was also possible to obtain left and right-handed helices according to the peptide fragment chirality (optically active materials). We were also able to produce a well defined fibril network with pore size controlled by polymer concentration, even to 100-250 nm. It was also possible to introduce efficiently reactive side groups in the chains. The polymers may therefore be used as a scaffold for biomolecules. We found that the porosity size is controlled by the concentration.

Examples of biomolecules are biologicals, proteins, glycoproteins, peptides, sugars, carbohydrates, lipoproteins, lipids, glycolipids, silicas, drugs, nucleic acids, DNA, RNA, vitamins, nutrients, hydrolysates, polysaccharides, monosaccharides, recombinant peptides, mucins, enzymes, bioorganic compounds, recombinant biomolecules, antibodies, hormones, growth factors, receptors, contrast agents, cytokines, and fragments and modifications thereof.

Cell Culture

The cell culture according to the invention comprises the hydrogel as described above. The cell culture is a three dimensional porous scaffold.

The invention further provides a process for making the cell culture according to the present invention, comprising the steps of: a) providing the oligo(alkylene glycol) functionalized co-polyisocyanopeptide, b) mixing the oligo(alkylene glycol) functionalized co-polyisocyanopeptide with a cell culture medium to obtain the hydrogel.

The cell culture can in principle be made with any type of cell culture medium suitable for the culturing of (animal) cells. Suitable cell culture media support the growth and differentiation of the cells used in the method of the invention.

Guidelines for choosing a cell culture medium and cell culture conditions are well known and are for instance provided in Chapter 8 and 9 of Freshney, R. I. Culture of animal cells (a manual of basic techniques), 4th edition 2000, Wiley-Liss and in Doyle, A., Griffiths, J. B., Newell, D. G. Cell & Tissue culture: Laboratory Procedures 1993, John Wiley & Sons.

Generally, a cell culture medium for (mammalian) cells comprises salts, amino acids, vitamins, lipids, detergents, buffers, growth factors, hormones, cytokines, trace elements, carbohydrates and other organic nutrients, dissolved in a buffered physiological saline solution. Examples of salts include magnesium salts, for example $MgCl_2.6H_2O$, $MgSO_4$ and $MgSO_4.7H_2O$ iron salts, for example $FeSO_4.7H_2O$, potassium salts, for example $KH_2PO_4$, KCl; sodium salts, for example $NaH_2PO_4$, $Na_2HPO_4$ and calcium salts, for example $CaCl_2.2H_2O$. Examples of amino acids are all 20 known proteinogenic amino acids, for example hystidine, glutamine, threonine, serine, methionine. Examples of vitamins include: ascorbate, biotin, choline.Cl, myo-inositol, D-panthothenate, riboflavin. Examples of lipids include: fatty acids, for example linoleic acid and oleic acid; soy peptone and ethanol amine. Examples of detergents include Tween 80 and Pluronic F68. An example of a buffer is HEPES. Examples of growth factors/hormones/cytokines include IGF, hydrocortisone and (recombinant) insulin. Examples of trace elements are known to the person skilled in the art and include Zn, Mg and Se. Examples of carbohydrates include glucose, fructose, galactose, sucrose and pyruvate.

The culture medium may be supplemented with growth factors, metabolites, etc.

Examples of suitable culture medium include Endothelial Growth Medium (EGM-2, Lonza, Walkersville, USA) fully supplemented with Getal Bovine Serum, Hydrcortisone, hFGF-B, VEGF, R3-IGF-1, Ascorbic Acid hEGF and GA-1000 and Smooth Muscle Cell Medium (SMCM, ScienCell, Carlsbad, USA) with the supplements including Fetal Bovine Serum, Smooth Muscle Cell Growth Supplement and Penicillin/Streptomycin.

The optimal conditions under which the cells are cultured can easily be determined by the skilled person. For example, the pH, temperature, dissolved oxygen concentration and osmolarity of the cell culture medium are in principle not critical and depend on the type of cell chosen. Preferably, the pH, temperature, dissolved oxygen concentration and osmolarity are chosen such that these conditions optimal for the growth and productivity of the cells. The person skilled in the art knows how to find the optimal pH, temperature, dissolved oxygen concentration and osmolarity. Usually, the optimal pH is between 6.6 and 7.6, the optimal temperature between 30 and 39° C., for example a temperature from 36 to 38° C., preferably a temperature of about 37° C.; the optimal osmolarity between 260 and 400 mOsm/kg.

The invention further provides a process for culturing cells, the process comprising the steps of:
a) providing the cell culture according to the invention,
b) adding the cells to the cell culture at a temperature below the gelation temperature of the hydrogel and
c) culturing the cells.

According to one aspect, the present invention provides a cell culture comprising a hydrogel comprising the oligo (alkylene glycol) functionalized co-polyisocyanopeptide, and at least one of endothelial cells and smooth muscle cells.

The cells are preferably co-cultured endothelial cells and smooth muscle cells. The concentration of the cells may e.g. be 2,000 cells/mL to 1,000,000 cells/mL. A 3-D structure, like for example a vascular system can be obtained thereby.

The invention further provides use of the cell culture according to the invention for making a prevascular system.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

DETAILED DESCRIPTION OF THE INVENTION

Experimental

Materials: Toluene was distilled over sodium. Dichloromethane was distilled over phosphorous pentoxide. N-methylmorpholine was freshly distilled over sodium prior to use. Water was purified with a Milipore MiliQ system, (mQ water 18.2 MΩ). All the other chemicals were used as received. Column chromatography was performed using silica gel (0.060-0.200 mm) provided by Baker. Thin layer chromatography (TLC) analyses were carried out on silica 60 $F_{254}$ coated glass obtained from Merck and the compounds were visualised using Ninhydrine or basic aqueous $KMnO_4$ solutions. All glassware was soaked in 0.5 M NaOH prior to use.

Example 1

Figure 2:
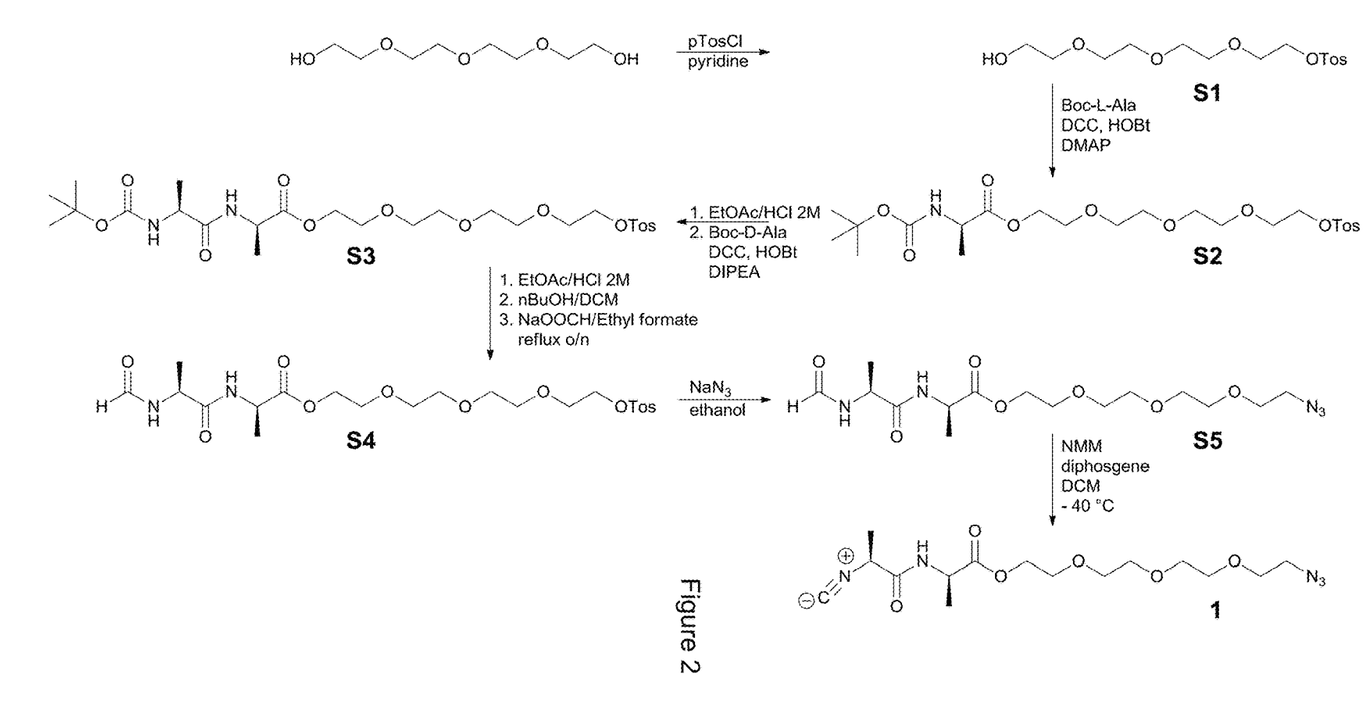
FIG. 2 is a scheme showing an example of the preparation route of an example of the first monomer.

(1) Preparation of the Copolymer
(1.1) Preparation of the First Comonomer
The first comonomer grafted with a linking group was synthesized according to the scheme of FIG. 2.

1.1.1. Synthesis of 2-(2-(2-(2-hydroxyethoxy)ethoxy)ethyl 4-methylbenzene sulfonate (S1)

Tetraethylene glycol (28.5 mL, 164.3 mmol) was dissolved in 50 mL pyridine. The solution was subsequently cooled to 0° C. while stirring. Argon was bubbled through the solution for 15 minutes. Tosylchloride (21.93 g, 115 mmol) was added portion wise to the stirring solution. The mixture was further stirred at room temperature for 12 hours. The reaction mixture was diluted with 50 mL of 10% citric acid. The mixture was extracted three times into 250 mL of chloroform. The combined organic layers were dried over anhydrous $Na_2SO_4$, filtered and evaporated under vacuum. The resulting yellow oil was purified using column chromatography ($SiO_2$, 0.060-0.200 mm; ethyl acetate as eluent) to yield S1 as a pale yellow oil (11.69 g, 33.6 mmol, 29%); $R_f$=0.4 (ethyl acetate).

FT-IR ($cm^{-1}$, ATR) 3442 (O—H), 2870 (C—H), 1597 (N—H), 1453 (C—H), 1352 (S=O), 1175 (S=O), 1096 (C—O); $^1$H NMR $\delta_H$ (300 MHz; $CDCl_3$; $Me_4Si$) 7.80 (dd, J=7.81 Hz, 2H, —C$\underline{H}_{Ar}$—), 7.33 (d, J=7.35 Hz, 2H, —C$\underline{H}_{Ar}$—S), 4.17 (m, 2H, O—C$\underline{H}_2$—C$\underline{H}_2$—), 3.65 (m, 16H, —C$\underline{H}_2$—), 2.45 (s, 3H, —C$\underline{H}_3$); $^{13}$C NMR $\delta_C$ (75 MHz; $CDCl_3$; $Me_4Si$) 21.16 (1C, $C$CH$_3$), 61.0 (1C, COH), 68.13 (1C, COS), 69.0 (1C, OCH$_2$), 70.0, 70.1, 70.1, 70.2 (4C, OCH$_2$), 70.8, 72.0 (2C, OCH$_2$), 127.5 (2C, CHCCH), 129.5 (2C, CHCCH), 139.7 (1C, CCH$_3$), 144.5 (1C, CHCS).

1.1.2. Synthesis of (R)-2-(2-(2-(2-(tosyloxy)ethoxy)ethoxy)ethyl 2-((tert-butoxycarbonyl)amino)propanoate (S2)

Compound S1 (5.23 g, 15.01 mmol), N-Boc-(L)-alanine (2.86 g, 15.01 mmol) and DMAP (0.198 g, 1.65 mmol) were dissolved in 25 mL of freshly distilled $CH_2Cl_2$ and cooled to 0° C. while stirring. DCC (3.12 g, 15.01 mmol) was added portion wise. The mixture turned yellow and was stirred for 1 h at 0° C. and therefore it was stirred for 3 h at room temperature. The precipitated dicyclohexyl urea was removed by filtration and washed with ethyl acetate (3×20 mL). The organic layer was concentrated under vacuum. The crude product was purified using column chromatography ($SiO_2$, 0.060-0.200 mm; 1% MeOH/$CH_2Cl_2$ as eluent) to yield S2 as a light orange oil (5.49 g, 11.4 mmol, 76%); $R_f$=0.4 (10% MeOH/$CH_2Cl_2$).

FT-IR ($cm^{-1}$, ATR) 2924 (C—H), 1745 (C=O ester), 1712 (C=O amide), 1597 (N—H), 1452 (C—H), 1352 (S=O), 1173 (S=O), 1120 (C—O); $^1$H NMR $\delta_H$ (300 MHz; $CDCl_3$; $Me_4Si$) 7.79 (d, J=8.4 Hz, 2H, —C$\underline{H}_{Ar}$—), 7.33 (d, J=8.1 Hz, 2H, —C$\underline{H}_{Ar}$—), 5.02 (s, 1H, —N$\underline{H}$—), 4.28 (m, 3H, —C$\underline{H}$(CH$_3$)—, COOC$\underline{H}_2$—), 4.15 (m, 2H, O—C$\underline{H}_2$—CH$_2$—), 3.69 (m, 14H, O—C$\underline{H}_2$—CH$_2$—), 2.44 (s, 3H, —C$\underline{H}_3$), 1.44 (s, 9H, —OC(C$\underline{H}_3$)$_3$), 1.37 (d, J=7.2 Hz, 3H, —CH(C$\underline{H}_3$)—); $^{13}$C NMR $\delta_C$ (75 MHz; $CDCl_3$; $Me_4Si$) 18.8 (1C, CHCH$_3$), 21.7 (1C, CCH$_3$), 28.4 (3C, C(CH$_3$)$_3$), 49.4 (1C, O(C=O)CHNH), 64.5 (1C, Boc-OCH$_2$), 68.9 (2C, OCH$_2$), 69.4 (1C, OCH$_2$), 70.7 (4C, OCH$_2$), 80.3 (1C, C(CH$_3$)$_3$), 128.2 (2C, CHCCH), 130.0 (2C, CHCCH), 145.0 (1C, CCH$_3$), 155.4 (1C, CHCS), 173.6 (1C, CH(C=O)NH), 176.7 (1C, CH(C=O)O); MS (ESI) m/z [M+Na]$^+$ calcd 542.2; found 542.2.

1.1.3. Synthesis of (R)-2-(2-(2-(2-(tosyloxy)ethoxy)ethoxy)ethyl 2-((S)-2-((tert-butoxycarbonyl)amino)propanamido)propanoate (S3)

Compound S2 (5.94 g, 11.4 mmol) was dissolved in 60 mL of HCl saturated ethyl acetate and stirred for 2 h at room temperature. The solvent was evaporated under vacuum and the excess HCl was removed by adding 30 mL of $CH_2Cl_2$ and 1 mL of n-BuOH followed by evaporation. The residual n-BuOH was removed via azeotropic distillation with 3×30 mL $CH_2Cl_2$. The resulting HCl salt of S2, N-Boc-(D)-alanine (2.14 g, 11.4 mmol) and N-hydroxybenzotriazole monohydrate (1.74 g, 11.4 mmol) were dissolved in 40 mL freshly distilled $CH_2Cl_2$. DIPEA (2 mL, 11.4 mmol) was added drop wise and the mixture was stirred at room temperature until everything was dissolved. The solution was cooled to 0° C. and DCC (2.35 g, 11.4 mmol) was added portion wise. A white precipitate was formed and the mixture was stirred for 1 h at 0° C. followed by 3 h of stirring at room temperature. The precipitate was filtered off, washed with ethyl acetate (3×30 mL) and the solvent was evaporated under vacuum. The crude product was purified using column chromatography (SiO$_2$, 0.060-0.200 mm; 2% MeOH/CH$_2$Cl$_2$ as eluent) to yield S3 as a pale yellow oil (3.37 g, 5.7 mmol, 52%); R$_f$=0.3 (10% MeOH/CH$_2$Cl$_2$).

FT-IR (cm$^{-1}$, ATR) 2876 (C—H), 1740 (C=O ester), 1718 (C=O amide), 1667 (N—H), 1522 (N—H), 1452 (C—H), 1365 (S=O), 1161 (S=O), 1105 (C—O); $^1$H NMR $\delta_H$ (300 MHz; CDCl$_3$; Me$_4$Si) 7.80 (d, J=8.4, 2H, —CH$_{Ar}$—C—S), 7.36 (d, J=8.1, 2H, —CH$_{Ar}$—), 6.91 (s, 1H, —NH), 5.00 (s, 1H, —NH), 4.58 (m, 1H, —NHCH(CH$_3$)—), 4.28 (m, 2H, —COOCH$_2$—), 4.14 (m, 2H, O—CH$_2$—CH$_2$—), 3.61 (m, 12H, —C(O)OCH$_2$CH$_2$O(CH$_2$CH$_2$O)$_3$—), 2.45 (s, 3H, —CH$_3$), 1.45 (s, 9H, —OC(CH$_3$)$_3$), 1.40 (d, J=7.2, 3H, —CH(CH$_3$)—), 1.35 (d, J=7.2, 3H, —CH(CH$_3$)—); $^{13}$C NMR $\delta_C$(75 MHz; CDCl$_3$; Me$_4$Si) 18.2 (2C, CHCH$_3$), 21.7 (1C, CCH$_3$), 28.4 (3C, C(CH$_3$)$_3$), 47.2 (1C, NCH), 50.0 (1C, NCH), 64.5 (1C, Boc-OCH$_2$), 68.7 (2C, OCH$_2$), 69.3 (1C, OCH$_2$), 70.6 (4C, OCH$_2$), 80.2 (1C, C(CH$_3$)$_3$), 128.0 (2C, CHCCH), 129.9 (2C, CHCCH), 133.1 (1C CCH$_3$), 144.9 (1C, CHCS), 172.7 (2C, C=O); MS (ESI) m/z [M+Na]$^+$ calcd 613.2; found 613.1.

1.1.4. Synthesis of (R)-2-(2-(2-(2-(tosyloxy)ethoxy)ethoxy)ethyl 2-((S)-2-formamidopropanamido)propanoate (S4)

Compound S3 (1.70 g, 2.85 mmol) was deprotected following the same procedure as described for compound S2 and used without further purification. The crude product was dissolved in 25 mL ethyl formate. Sodium formate (0.97 g, 14.25 mmol) was added and the mixture was heated for 8 hours at 66° C. The mixture was cooled to room temperature and the solid was filtered-off. The solvent was evaporated under vacuum. The crude product was purified using column chromatography (SiO$_2$, 0.060-0.200 mm; 4% MeOH/CH$_2$Cl$_2$ as eluent) to yield S4 as a light yellow oil (0.79 g, 1.52 mmol, 54%); R$_f$=0.3 (10% MeOH/CH$_2$Cl$_2$).

FT-IR (cm$^{-1}$, ATR) 2873 (C—H), 1738 (C=O), 1653 (N—H), 1532 (N—H), 1452 (C—H), 1352 (S=O), 1174 (S=O), 1097 (C—O); $^1$H NMR $\delta_H$ (300 MHz; CDCl$_3$; Me$_4$Si) 8.18 (s, 1H, HC(O)NH—), 7.79 (d, J=8.4, 2H, —CH$_{Ar}$—C—S), 7.35 (d, J=8.7, 2H, —CH$_{Ar}$—), 6.78 (s, 1H, —NH), 6.55 (s, 1H, —NH), 4.55 (m, 2H, —NHCH(CH$_3$)—), 4.30 (m, 2H, —COOCH$_2$—), 4.13 (m, 2H, O—CH$_2$—CH$_2$—), 3.61 (m, 12H, —(CH$_2$CH$_2$O)$_3$—), 2.44 (s, 3H, —CH$_3$), 1.42 (m, 6H, —CH(CH$_3$)—); $^{13}$C NMR $\delta_C$ (75 MHz; CDCl$_3$; Me$_4$Si) 17.9 (1C, CHCH$_3$), 18.2 (1C, CHCH$_3$), 21.7 (1C, CCH$_3$), 47.2 (1C, O(C=O)HNCH), 48.1 (1C, HNHC(C=O)), 64.5 (1C, OCH$_2$), 68.7 (2C, OCH$_2$), 69.3 (1C, OCH$_2$), 70.6 (4C, OCH$_2$), 128.0 (2C, CHCCH), 129.9 (2C, CHCCH), 133.1 (1C, CCH$_3$), 144.9 (1C, CHCCH), 161.0 (1C, H(C=O)NH)), 172.6 (1C, CH(C=O)NH), 173.2 (1C, CH(C=O)O); MS (ESI) m/z [M+Na]$^+$ calcd 541.2; found 541.2.

1.1.5. Synthesis of (R)-2-(2-(2-(2-azidoethoxy)ethoxy)ethoxy)ethyl 2-((S)-2-formamido propanamido)propanoate (S5)

Compound S4 (0.550 g, 1.06 mmol) was dissolved in 40 mL of absolute EtOH. Sodium azide (0.38 g, 5.9 mmol) was added and the mixture was refluxed overnight. Once cooled to room temperature, the solids were removed by filtration and the filtrate was dried under vacuum. The crude product was purified using column chromatography (SiO$_2$, 0.060-0.200 mm; 4% MeOH/CH$_2$Cl$_2$ as eluent) to yield S5 as a pale pale orange oil (0.32 g, 0.82 mmol, 78%); R$_f$=0.4 (10% MeOH/CH$_2$Cl$_2$).

FT-IR (cm$^{-1}$, ATR) 3309 (N—H), 2875 (C—H), 2105 (N3), 1737 (C=O), 1651 (N—H), 1529 (N—H), 1453 (C—H), 1133 (C—O); $^1$H NMR $\delta_H$ (300 MHz; CDCl$_3$; Me$_4$Si) 8.20 (s, 1H, HC(O)NH—), 6.84 (s, 1H, —NH), 6.60 (s, 1H, —NH), 4.60 (m, 2H, NHCH(CH$_3$)), 4.26 (m, 2H, —C(O)OCH$_2$—), 3.68 (m, 12H, —(CH$_2$CH$_2$O)$_3$—), 3.40 (m, 2H, N$_3$CH$_2$—), 1.42 (m, 6H, —CH(CH$_3$)—); $^{13}$C NMR $\delta_C$ (75 MHz; CDCl$_3$; Me$_4$Si) 17.9 (1C, CH$_3$), 18.2 (1C, CH$_3$), 47.4 (1C, CH$_2$N$_3$), 48.4 (1C, H(C=O)HNCH), 50.7 (1C, HNC(CH$_3$)C=O), 69.0 (1C, CH$_2$CH$_2$O), 70.1 (1C, OCH$_2$CH$_2$), 70.6 (2C, OCH$_2$), 70.7 (2C, OCH$_2$), 161.4 (1C, H(C=O)NH), 172.7 (1C, CH(C=O)NH), 172.9 (1C, CH(C=O)O); MS (ESI) m/z [M+Na]$^+$ calcd 412.2; found 412.2.

1.1.6. Synthesis of (R)-2-(2-(2-(2-azidoethoxy)ethoxy)ethoxy)ethyl 2-((S)-2-isocyanopropanamido)propanoate (1)

Compound S5 (221 mg, 0.57 mmol) and N-methylmorpholine (0.24 mL, 2.27 mmol) were dissolved in 150 mL freshly distilled CH$_2$Cl$_2$ and cooled down to −40° C. (dry acetone bath) under an argon atmosphere. A solution of diphosgene (0.048 mL, 0.398 mmol) in 10 mL of freshly distilled CH$_2$Cl$_2$ was added drop wise under argon over 1 h. While adding diphosgene, the mixture was stirred and kept strictly at −40° C. Once the mixture began to turn yellow, the reaction was rapidly quenched with an excess of sodium bicarbonate (5 g). The quenched mixture was stirred for 5 minutes at −40° C. The reaction mixture was passed over a short silica columnplug (SiO$_2$, 0.060-0.200 mm). The plug was packed with CH$_2$Cl$_2$ but the desired compound was eluted with CH$_2$Cl$_2$/acetonitrile (3:1) to yield 1 as a pale yellow oil (48.1 mg, 0.48 mmol, 27%); R$_f$=0.5 (10% MeOH/CH$_2$Cl$_2$).

FT-IR (cm$^{-1}$, ATR) 3318 (N—H), 2875 (C—H), 2142 (C≡N), 2105 (N3), 1744 (C=O), 1540 (N—H), 1453 (C—H), 1123 (C—O); $^1$H NMR $\delta_H$ (300 MHz; CDCl$_3$; Me$_4$Si) 7.00 (bd, 1H, —NH—), 4.59 (m, 1H, —NHCH(CH$_3$)C(O)O—), 4.32 (m, 3H, —C(O)OCH$_2$CH$_2$O—), —C≡NCH(CH$_3$)C(O)NH—), 3.67 (m, 12H, —(OCH$_2$CH$_2$)$_3$), 3.39 (m, 2H, N$_3$CH$_2$—), 1.65 (d, J=7.2, 3H, C≡NCH(CH$_3$)C(O)—), 1.48 (d, J=7.2, 3H, C≡NCH(CH$_3$)C(O)—); $^{13}$C NMR $\delta_C$ (75 MHz; CDCl$_3$; Me$_4$Si) 170.69 (1C, CH(CH$_3$)C(O)OCH$_2$), 165.72 (1C, CH(CH$_3$)C(O)NH), 70.69, 70.65, 70.61, 70.56, 70.02, 68.81 (1C, CH$_2$CH$_2$O), 50.66 (1C, CH$_2$N$_3$), 48.56 (C≡NCH), 19.66, 18.04 (1C, CH(CH$_3$)CO); MS (ESI) m/z [M+Na]$^+$ (C$_{15}$H$_{25}$N$_5$O$_6$Na), calcd 394.17; found 394.1.

(2.1) Preparation of the Second Comonomer

Figure 3:
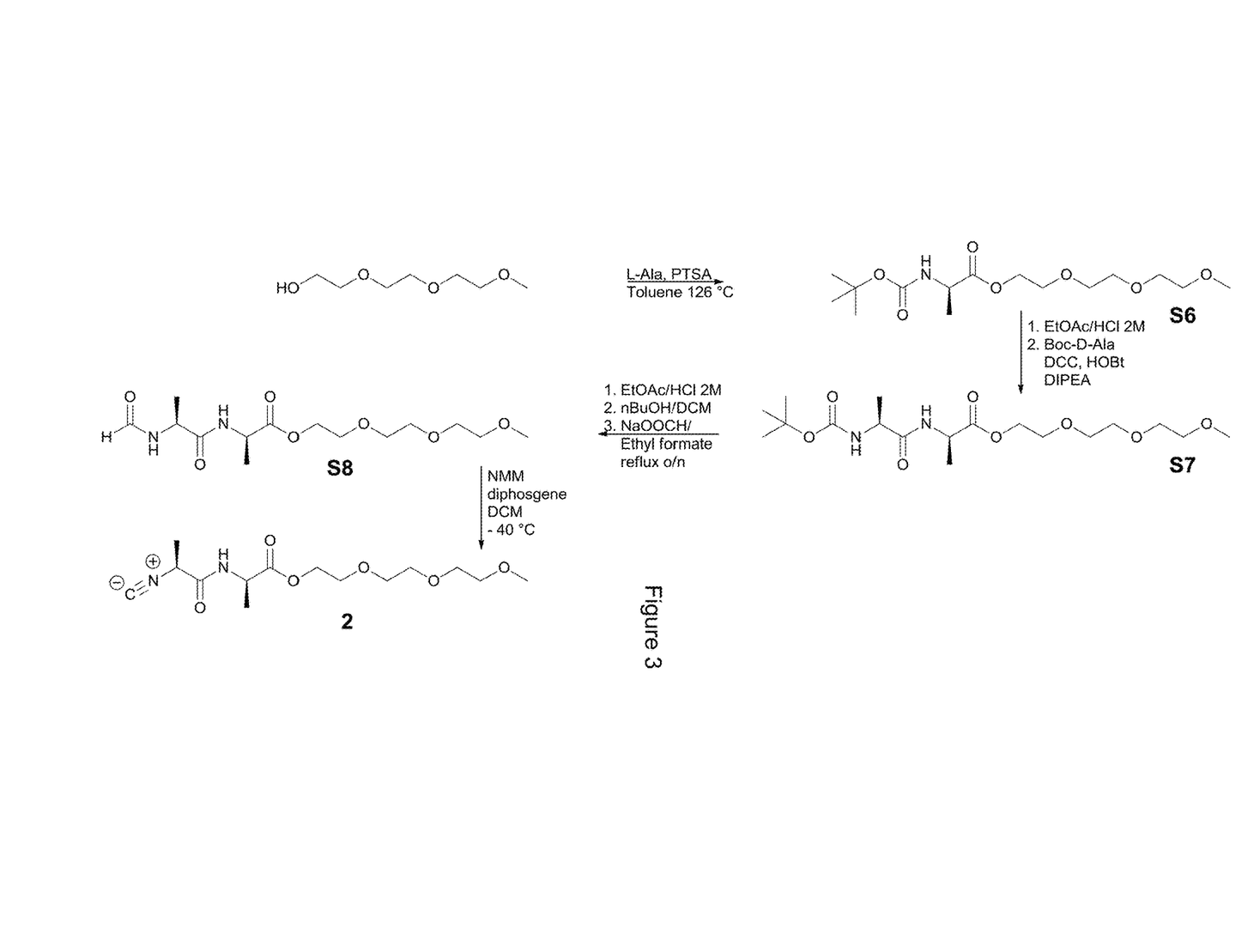
FIG. 3 is a scheme showing an example of the preparation route of an example of the second monomer.

The second comonomer which is not grafted with linking group was synthesized according to the scheme of FIG. 3.

2.1.1 Synthesis of 2-(2-(2-methoxyethoxy)ethoxy)ethyl 2-aminopropanoate (S6)

Triethylenglycol methoxy (25 ml, 156.21 mmol), L-alanine (21.85 g, 245.25 mmol), p-toluene sulfonic acid (32.69 g, 171.83 mmol) and 250 ml of toluene were added in a round bottom flask. The reaction mixture was refluxed at 126 OC for 4 h. A solid precipitate was filtered off, and the solvent was evaporated under reduced pressure. Then the product was dissolved with 300 ml of chloroform, and the organic layer was extracted three times with NaHCO$_3$ (saturated). Thereafter, the water layer was extracted twice with chloroform. The organic layers were dried with Na$_2$SO$_4$, and the solvent was evaporated under reduced pressure, obtaining 22.69 g of S6 with a 62% yield.

2.1.2 Synthesis of 2-(2-(2-methoxyethoxy)ethoxy) ethyl 2-((tert-butoxycarbonyl)amino)propanoate (S7)

Boc-D-Ala-OH (18.25 g, 96.44 mmol), DMAP (0.1 g, 0.8 mmol), DiPEA (1.7 ml, 9.64 mmol), HoBt (14.77 g, 96.44 mmol), DCC (21.89 g, 106.08 mmol), S6 (22.69 g, 96.44 mmol) and 250 ml of CH$_2$Cl$_2$ were mixed together, cooled in a ice bath to 0° C. and stirring for 3 hours. Thereafter, the mixture was allowed to reach room temperature and stirred for 15 h. The solid was filtered off, the product was dissolved with 200 ml of chloroform, and the solution was extracted with citric acid three times. The water layer was washed with chloroform (1×200 ml). The organic layer was washed with saturated NaHCO$_3$ solution twice, and the water layer was extracted with chloroform two more times. The organic layers were combined and dried with Na$_2$SO$_4$, and the solvent was evaporated under reduced pressure. Column chromatography (2% MeOH in CH$_2$Cl$_2$) was used to purify the crude product, obtaining 20.4 g of S7 in a 52% yield.

R$_f$=0.53 (10% MeOH/CH$_2$Cl$_2$)) $^1$H NMR (CDCl$_3$, 400 MHz): δ=6.77 (s, 1H, —NHCH—); 5.09 (s, 1H, —NHCH)—; 4.60 (q, 1H, —NHCH(CH$_3$)—); 4.31-4.28 (m, 3H, —C(O)OCH$_2$CH$_2$O—, —CH(CH$_3$)COO—); 3.70-3.56 (m, 10H, —C(O)OCH$_2$CH$_2$O(CH$_2$CH$_2$O)$_2$—); 3.38 (s, 1H, —OCH$_3$); 1.46 (s, 9H, —OC(CH$_3$)$_3$); 1.41 (d, 3H, —NHCH(CH$_3$)—; 1.38 (d, 3H, —NHCH(CH$_3$)—)

S7 (13.15 g, 32.35 mmol) was dissolved in 20 ml of ethyl acetate and treated with 20 ml of 4 M HCl in dioxane. The mixture was stirred for 1 hour at room temperature. After checking via TLC with starting compound another 20 ml 4 M HCl in dioxane was added and the solution was stirred further for 1 hour at room temperature. The residual t-BuOH was removed by addition of 20 mL of DCM and removed under reduced pressure. This procedure was repeated three times.

2.1.3 Synthesis of 2-(2-(2-methoxyethoxy)ethoxy)ethyl 2-formamidopropanoate (S8)

The HCl salt of S7 (13.15 g, 32.33 mmol) and sodiumformate (8.76 g, 129.33 mmol) were dissolved into 250 ml of ethylformate. The reaction mixture was boiled for 14 h at 66 OC. A precipitate was filtered off, and the solvent was evaporated under reduced pressure. Column chromatography (4% MeOH in CH$_2$Cl$_2$) was used to purify the crude product, obtaining 6.04 g of S8 in a 56% yield.

R$_f$=0.54 (10% MeOH/CH$_2$Cl$_2$) $^1$H NMR (CDCl$_3$, 400 MHz): δ=8.23 (s, 1H, HC(O)NH—); 6.94 (d, 1H, —NHCH—); 6.79 (d, 1H, —NHCH—; 4.57 (m, 2H, NHCH(CH$_3$)—, —NHCH(CH$_3$)—); 4.26 (m, 2H, —C(O)OCH$_2$—); 3.67-3.54 (m, 10H, —C(O)OCH$_2$CH$_2$O(CH$_2$CH$_2$O)$_3$—); 3.43 (s, 3H, —OCH$_3$); 1.45 (t, 6H, —NHCH(CH$_3$)—, —NHCH(CH$_3$)—

2.1.4 Synthesis of 2-(2-(2-methoxyethoxy)ethoxy)ethyl 2-isocyanopropanoate (2)

S8 (6.04 g, 18.06 mmol) was degassed for 1 hour with N$_2$. Then NMM (5 ml, 45.15 mmol) was dissolved with freshly distilled CH$_2$Cl$_2$ (50 ml), and added to the solution. The reaction mixture was cooled to −40 ° C. (dry ice/isopropanol). A solution of diphosgene (1.52 ml, 12.64 mmol) in CH$_2$Cl$_2$ (50 ml) was added dropwise over 2 h. The reaction mixture was stirred until it turned a yellow-orange colour, and quenched with NaHCO$_3$ (3 g). Column chromatography (1:2 ACN/CH$_2$Cl$_2$) was used to purify the crude product, obtaining 3.34 g of 2 in a 51% yield.

R$_f$=0.50 (10% MeOH/CH$_2$Cl$_2$) $^1$H NMR (CDCl$_3$, 400 MHz): δ=7.00 (d, 1H, —NH—); 4.58 (m, 1H, C≡NCH(CH$_3$)C(O)NH—); 4.28 (m, 2H, —C(O)OCH$_2$CH$_2$O—); 4.26 (m, 1H, —NHCH(CH$_3$)C(O)O—); 3.74-3.53 (m, 10H, —OCH$_2$CH$_2$ (OCH$_2$CH$_2$)$_3$OCH$_3$); 3.41 (s, 3H, —OCH$_3$); 1.67 (d, 3H, C≡NCH(CH$_3$)C(O)—); 1.49 (d, 3H, —NHCH(CH$_3$)C(O)O—)

(3) Polymerization

Compound 2 (e.g. 100 eq) and Compound 1 (1 eq) were dissolved in 2 mL of distilled toluene. The catalyst stock solution of 1 mM was prepared by dissolving 39 mg of Ni(Cl$_2$O$_4$)$_2$·6H$_2$O in 10 mL of absolute ethanol and 90 mL of toluene. A volume equal to a total monomer mole×10$^{-4}$ was pipette to the monomers. The mixture was diluted with distilled toluene to obtain a final concentration of 25 mg/mL monomer. The mixture was stirred for 72 h at room temperature in a flask fitted with a CaCl$_2$ drying tube. The polymer was isolated via precipitation into diisopropylether. This precipitation cycle was repeated three times to obtain yields varying from 44-92% yield. Polymers were analysed by measuring the intrinsic viscosity, rheology (G') and circular dichroism and they were visualized by dropcasting from solution onto mica via AFM.

(4) Grafting of Spacer Unit/Cell Adhesion Unit to the Copolymer

A peptide (GRGDS) was dissolved in borate buffer pH 8.4 to a final concentration of 2 mg/mL. A spacer unit represented by formula (III) (BCN-NHS) was added in a 1:1 molar ratio to the peptide solution and mixed 300 rpm 18° C. at for one hour before being frozen in 100 uL aliquots. BCN-GRGDS represented by formula (V) was obtained. MS calc [C$_{39}$H$_{62}$N$_{10}$O$_{15}$]: 910.4 obtained: 911.5.

The polyisocyanide (PIC) obtained in the previous step was dissolved in ACN at 2 mg/mL. To this PIC solution the appropriate volume of BCN-GRGDS based on the molar equivalent of azide co-monomer in the polyisocyanide backbone, was added. The mixture was allowed to stir for 72 hours at 4° C. The PIC-peptide was purified by precipitated from diisopropyl ether. The precipitant was decanted and the polyisocyanide-peptide re-dissolved and precipitated from DCM into diisopropyl ether.

(5) Preparation of the Hydrogel from the Copolymer

From this point forward care was taken to ensure that the polyisocyano-peptide remained sterile. All equipment was sprayed with ethanol before use. The PIC-peptide conjugate was weighted directly into a sterile centrifuge tube. The tubes were further sterilized by exposing them to UV radiation for a period of 5 minutes. The PIC-peptide was covered with sterile cell culture medium to obtain the final dilution of polymer in media of 3.2 mg/mL and allowed to swell for 24 hours at 4° C. After 24 hours a swollen gel like substance was obtained at the bottom of the centrifuge tube. The swollen PIC-peptide conjugate was stirred for 72 hours at 4 C after which a uniform solution was obtained. The solution exhibited a sharp transition in viscosity above the critical temperature.

The PIC-peptide conjugates in medium remained stable for up to 20 months at 4-7° C. or for longer periods when frozen.

For the preparation of prevascularisation constructs of appropriate stiffness and concentration the stock solution of gel at 3.2 mg/mL was diluted with an appropriate amount of medium to reach the desired final concentration of polymer, which was 2.0 mg/mL.

(6) Preparation of the Hydrogel Comprising the Cells (6-1) Preparation of the Cell Medium Comprising the Cells HUVECs (ACTT, PCS-100-010, USA) were expanded in Endothelial Growth Medium (EGM-2, Lonza, Walkersville, USA) fully supplemented with Getal Bovine Serum, Hydrocortisone, hFGF-B, VEGF, R3-IGF-1, Ascorbic Acid hEGF and GA-1000. HbSMCs (ScienCell, 4310, Carlsbad, USA) were expanded in Smooth Muscle Cell Medium (SMCM, ScienCell, Carlsbad, USA) with the supplements including Fetal Bovine Serum, Smooth Muscle Cell Growth Supplement and Penicillin/Streptomycin. These two cell types were expanded in T75 flask (Corning Incorporated, Corning, USA) in 5% CO2 at 37° C. Medium was changed three times per week and cells were harvest with trypsin treatment. HbSMCs of passage 8 and HUVECs of passage 9 were used by all experiments.

(6-2) Mixing the Hydrogel and the Cell Medium Comprising the Cells

For the production of the prevascularization constructs the temperature of the solution of the thermoresponsive PIC-peptide conjugate as obtained in step (B) was lowered to 0° C. to induce a gel to liquid transition. Subsequently, an aliquot of the liquefied gel was mixed with the cell-suspension containing both HUVECs and HbSMCs as obtained in step (6-1) to create the desired concentration of cells of 500,000 cells/ml. Aliquots of 200 µl of these gel-cell suspensions were subsequently transmitted to 24-well inserts (membrane pore size of 0.2 µm) and placed for 30 minutes at 37° C. to assure solidification of the gel.

(7) Culturing of the Cells to Form a Prevascular System

It was observed that the cells attach to the hydrogel within 3 days and vascularisation was observed within 7 days.

The produced prevascularization constructs were cultured in a suitable mixture of media in 5% CO2 at 37° Celsius for 14 days. Progress of vascularisation constructs was followed.

Comparative Experiment 2 (Low Polymer Concentration)

Example 1 was repeated except that the polymer concentration in step (5) was 1.0 mg/mL instead of 2.0 mg/mL.

In step (7), after the solidification of the gel, the cells gradually sank to the bottom of the 24-well inserts. Some clustering a sprouting of the cells was observed however the structures formed were of poor quality. The experiments were terminated after 3 days. No prevascular system was formed.

Comparative Experiment 3 (High Polymer Concentration)

Example 1 was repeated except that the polymer concentration in step (5) was 3.2 mg/mL instead of 2.0 mg/mL.

In step (7), progress of vascularisation constructs was observed although very slowly. The cells remained suspended in the 24-well inserts. Cells remained spherical in shape from day 1-7 after which the onset of sprouting was observed. The experiment was terminated after 14 days. The cell structures formed appeared to be of poor quality and no prevascular system was formed. It appeared that the hydrogel was too stiff for these particular cells to move/grow within the gel efficiently From the comparison of Example 1 and comparative experiment 2 and 3, it can be concluded that the concentration of the copolymer in the hydrogel is important for the formation of the vascularisation constructs. A suitable concentration range is 1.2-3.0 mg/mL.

Comparative Experiment 4 (Too Little Grgds)

Example 1 was repeated except that the ratio between compound 1 and compound 2 and in step (3) was 1:550 instead of 1:100.

In step (7), after the solidification of the gel, cells remained spherical for an extended period limited sprouting was observed prevascularisation was not complete following 21 days. No prevascular system was formed.

Comparative Experiment 5 (Too Much Grgds)

Example 1 was repeated except that the ratio between compound 2 and compound 1 in step (3) was 1:25 instead of 1:100.

In step (7), after the solidification of the gel, uncontrolled and undirected cell growth was observed the structures formed did not represent a prevascular system.

Comparative Experiment 6 (Too Much Grgds)

Example 1 was repeated except the ratio between compound 2 and compound 1 in step (3) was 1:10 instead of 1:100.

In step (5), after PIC-peptide was covered with sterile cell culture medium, no gel like substance was obtained and the experiment was terminated.

From the comparison of Example 1 and comparative experiment 4 and 5, it can be concluded that the ratio of the comonomer grafted with GRGDS is important for the formation of the vascularisation constructs. The suitable ratio is 1:550-1:50.

Experiment 7

The elastic modulus of the hydrogel obtained in step 5 of Example 1 was measured as follows:

Instrumental. Rheological measurements were performed using a TA Instruments Ares G2 rheometer in a ≈20 mL Couette configuration with temperature control using a peltier element. Samples were prepared by mixing the appropriate amount of polymer in demi water (20 mL) and regular vortexing the mixture over time (at least 24 hours) until a homogeneous solution was obtained. Solutions of PIC were prepared in refrigerated (4° C.) conditions to avoid early gel formation. The measurements in the linear response regime were conducted at 4% strain at different frequencies between 0.5 and 5 Hz. The data depicted in the manuscript was recorded at 1 Hz. Temperature scans were recorded at a heating rate of 2° C. $\min^{-1}$. The measurements in biologically relevant medias was performed on a TA Instruments Discovery HR-1 40 mm Aluminium parallel plate, set to a gap of 750 um and 1 mL of sample. The temperature controlled using a peltier element and evaporation guard. PIC samples were prepared by mixing the appropriate amount of polymer in DMEM and regular stirring continuously at 4° C. (at least 48 hours) until a homogeneous solution was obtained. Solutions of PIC were used directly or frozen until measurements could be pre- formed to avoid sample memory effects. The matrigel was used as is from supplier and the fibrin gels were prepared by dissolving fibrinogen in DMEM, containing FBS and allowed to gelate for 2 hours at 37° C. before measurement. The measurements in the linear response regime were conducted at 2% strain at different frequencies between 1 Hz. Temperature scans were recorded at a heating or cooling rate of 2° C. $min^{-1}$.

The elastic modulus was substantially constant at the temperature range of 5-15° C. and was measured to be around 1 Pa. The elastic modulus increased to around 100 Pa by 23° C. The elastic modulus increased to around 500 Pa by 35° C.

What is claimed is:

1. A process for making an oligo(alkylene glycol) functionalized co-polyisocyanopeptide, wherein the process comprises the steps of:
   i) copolymerizing
      a first comonomer of an oligo(alkylene glycol) functionalized isocyanopeptide grafted with a linking group and
      a second comonomer of a non-grafted oligo(alkylene glycol) functionalized isocyanopeptide,
      wherein a molar ratio between the first comonomer and the second comonomer is 1:500 and 1:30 and
   ii) adding a reactant of a spacer unit and a cell adhesion factor to the copolymer obtained by step i), wherein the spacer unit is represented by general formula A-L-B,
   wherein the linking group and group A are chosen to react and form a first coupling and the cell adhesion factor and group B are chosen to react and form a second coupling,
   wherein the first coupling and the second coupling are independently an alkyne-azide coupling, dibenzocyclooctyne-azide coupling, oxanorbornadiene-based-azide couplings, vinylsulphone-thiol coupling, maleimide-thiol coupling, methyl methacrylate-thiol coupling, ether coupling, thioether coupling, biotin-strepavidin coupling, amine-carboxylic acid resulting in amides linkages, alcohol-carboxylic acid coupling resulting in esters linkages or NHS-Ester (N-Hydroxysuccinimide ester)-amine coupling and
   wherein group L is a linear chain segment having 10-60 bonds between atoms selected from C, N, O and S in the main chain.

2. The process according to claim 1, wherein group L is chosen from:

where p is 1 to 10, or where q is 1 to 9, or where r is 1 to 10.

3. The process according to claim 1, wherein the first coupling is the alkyne-azide coupling.

4. The process according to claim 1, wherein the second coupling is the NHS-ester (N-Hydroxysuccinimide ester)-amine coupling or the maleimide-thiol coupling.

5. The process according to claim 1, wherein group A is represented by formula (VII):

(VII)

wherein:

n is 0 to 8;

$R^3$ is $[(L)_p-Q]$, hydrogen, halogen, $C_1-C_{24}$ alkyl groups, $C_6-C_{24}$ (hetero)aryl groups, $C_7-C_{24}$ alkyl(hetero)aryl groups or $C_7-C_{24}$ (hetero)arylalkyl groups, the alkyl groups optionally being interrupted by one of more hetero-atoms selected from the group consisting of O, N and S, wherein the alkyl groups, (hetero)aryl groups, alkyl(hetero)aryl groups and (hetero)arylalkyl groups are independently optionally substituted with one or more substituents independently selected from $C_1-C_{12}$ alkyl groups, $C_2-C_{12}$ alkenyl groups, $C_2-C_{12}$ alkynyl groups, $C_3-C_{12}$ cycloalkyl groups, $C_1-C_{12}$ alkoxy groups, $C_2-C_{12}$ alkenyloxy groups, $C_2-C_{12}$ alkynyloxy groups, $C_3-C_{12}$ cycloalkyloxy groups, halogens, amino groups, oxo groups and silyl groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from O, N and S, wherein the silyl groups are represented by the formula $(R^4)_3Si—$, wherein $R^4$ is independently selected from $C_1-C_{12}$ alkyl groups, $C_2-C_{12}$ alkenyl groups, $C_2-C_{12}$ alkynyl groups, $C_3-C_{12}$ cycloalkyl groups, $C_1-C_{12}$ alkoxy groups, $C_2-C_{12}$ alkenyloxy groups, $C_2-C_{12}$ alkynyloxy groups and $C_3-C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from O, N and S;

$R^1$ is independently selected from hydrogen, $C_1-C_{24}$ alkyl groups, $C_6-C_{24}$ (hetero)aryl groups, $C_7-C_{24}$ alkyl(hetero)aryl groups and $C_7-C_{24}$ (hetero)arylalkyl groups; and $R^2$ is independently selected from halogen, $—OR^6$, $—NO_2$, $—CN$, $—S(O)_2R^6$, $C_1-C_{12}$ alkyl groups, $C_1-C_{12}$ aryl groups, $C_1-C_{12}$ alkylaryl groups and $C_1-C_{12}$ arylalkyl groups, and wherein the alkyl groups, aryl groups, alkylaryl groups and arylalkyl groups are optionally substituted;

L is a linking group selected from linear or branched $C_1-C_{24}$ alkylene groups, $C_2-C_{24}$ alkenylene groups, C$_2$-C$_{24}$ alkynylene groups, C$_3$-C$_{24}$ cycloalkylene groups, C$_5$-C$_{24}$ cycloalkenylene groups, C$_8$-C$_{24}$ cycloalkynylene groups, C$_7$-C$_{24}$ alkyl(hetero)arylene groups, C$_7$-C$_{24}$ (hetero)arylalkylene groups, C$_8$-C$_{24}$ (hetero)arylalkenylene groups, C$_9$-C$_{24}$ (hetero)arylalkynylene groups, the alkylene groups, alkenylene groups, alkynylene groups, cycloalkylene groups, cycloalkenylene groups, cycloalkynylene groups, alkyl(hetero)arylene groups, (hetero)arylalkylene groups, (hetero)arylalkenylene groups and (hetero)arylalkynylene groups optionally being substituted with one or more substituents independently selected from the group consisting of C$_1$-C$_{12}$ alkyl groups, C$_2$-C$_{12}$ alk- enyl groups, C$_2$-C$_{12}$ alkynyl groups, C$_3$-C$_{12}$ cycloalkyl groups, C$_5$-C$_{12}$ cycloalkenyl groups, C$_8$-C$_{12}$ cycloalkenyl groups, C$_1$-C$_{12}$ alkoxy groups, C$_2$-C$_{12}$ alkenyloxy groups, C$_2$-C$_{12}$ alkynyloxy groups, C$_3$-C$_{12}$ cycloalkyloxy groups, halogens, amino groups, oxo and silyl groups, wherein the silyl groups can be represented by the formula (R$^4$)$_3$Si—, wherein R$^4$ is defined as above;

Q is a functional group selected from the group consisting of hydrogen, halogen, R$^6$, —CH=C(R$^6$)$_2$, —C≡CR$^6$, —[C(R$^6$)$_2$C(R$^6$)$_2$O]$_q$—R$^6$, wherein q is in the range of 1 to 200, —CN, —N$_3$, —NCX, —XCN, —XR$^6$, —N(R$^6$)$_2$, —$^+$N(R$^6$)$_3$, —C(X)N(R$^6$)$_2$, —C(R$^6$)$_2$XR$^6$, —C(X)R$^6$, —C(X)XR$^6$, —S(O)R$^6$, —S(O)2R$^6$, —S(O)OR$^6$, —S(O)2OR$^6$, —S(O)N(R$^6$)$_2$, —S(O)$_2$N(R$^6$)$_2$, —OS(O)R$^6$, —OS(O)$_2$R$^6$, —OS(O)OR$^6$, —OS(O)$_2$OR$^6$, —P(O)(R$^6$)(OR$^6$), —P(O)(OR$^6$)$_2$, —OP(O)(OR$^6$)$_2$, —Si(R$^6$)$_3$, —XC(X)R$^6$, —XC(X)XR$^6$, —XC(X)N(R$^6$)$_2$, —N(R$^6$)C(X)R$^6$, —N(R$^6$)C(X)XR$^6$ and —N(R$^6$)C(X)N(R$^6$)$_2$, wherein X is oxygen or sulphur;

R$^6$ is independently selected from the group consisting of hydrogen, halogen, C$_1$-C$_{24}$ alkyl groups, C$_6$-C$_{24}$ (hetero)aryl groups, C$_7$-C$_{24}$ alkyl(hetero)aryl groups and C$_7$-C$_{24}$ (hetero)arylalkyl groups; and wherein p is 0 or 1.

6. The process according to claim 5, wherein the spacer unit is represented by formula (IX):

wherein R$^1$, R$^2$, R$^3$ and n are as defined in claim 5 and

L is selected from the group represented by formula (X):

wherein p is 2 to 5.

7. The process according to claim 1, wherein the spacer unit is represented by formula (XI):

wherein p is 2 to 5.

8. The process according to claim 1, wherein the average of the number of the alkylene glycol units on the first comonomer and the second comonomer is at least 3 and at most 4.

9. The process according to claim 2, wherein the first coupling is alkyne-azide coupling.

10. The process according to claim 9, wherein the second coupling is the NHS-ester (N-Hydroxysuccinimide ester)-amine coupling or the maleimide-thiol coupling, wherein group A is represented by formula (VII):

wherein:
n is 0 to 8;
R$^3$ is [(L)$_p$-Q], hydrogen, halogen, C$_1$-C$_{24}$ alkyl groups, C$_6$-C$_{24}$ (hetero)aryl groups, C$_7$-C$_{24}$ alkyl(hetero)aryl groups or C$_7$-C$_{24}$ (hetero)arylalkyl groups, the alkyl groups optionally being interrupted by one of more hetero-atoms selected from the group consisting of O, N and S, wherein the alkyl groups, (hetero)aryl groups, alkyl(hetero)aryl groups and (hetero)arylalkyl groups are independently optionally substituted with one or more substituents independently selected from C$_1$-C$_{12}$ alkyl groups, C$_2$-C$_{12}$ alkenyl groups, C$_2$-C$_{12}$ alkynyl groups, C$_3$-C$_{12}$ cycloalkyl groups, C$_1$-C$_{12}$ alkoxy groups, C$_2$-C$_{12}$ alkenyloxy groups, C$_2$-C$_{12}$ alkynyloxy groups, C$_3$-C$_{12}$ cycloalkyloxy groups, halogens, amino groups, oxo groups and silyl groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of o e hetero-atoms selected from O, N and S, wherein the silyl groups are represented by the formula $(R^4)_3Si$—, wherein $R^4$ is independently selected from $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from O, N and S;

$R^1$ is independently selected from hydrogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups; and $R^2$ is independently selected from halogen, —$OR^6$, —$NO_2$, —CN, —$S(O)_2R^6$, $C_1$-$C_{12}$ alkyl groups, $C_1$-$C_{12}$ aryl groups, $C_1$-$C_{12}$ alkylaryl groups and $C_1$-$C_{12}$ arylalkyl groups, and wherein the alkyl groups, aryl groups, alkylaryl groups and arylalkyl groups are optionally substituted;

L is a linking group selected from linear or branched $C_1$-$C_{24}$ alkylene groups, $C_2$-$C_{24}$ alkenylene groups, $C_2$-$C_{24}$ alkynylene groups, $C_3$-$C_{24}$ cycloalkylene groups, $C_5$-$C_{24}$ cycloalkenylene groups, $C_8$-$C_{24}$ cycloalkynylene groups, $C_7$-$C_{24}$ alkyl(hetero)arylene groups, $C_7$-$C_{24}$ (hetero)arylalkylene groups, $C_8$-$C_{24}$ (hetero)arylalkenylene groups, $C_9$-$C_{24}$ (hetero)arylalkynylene groups, the alkylene groups, alkenylene groups, alkynylene groups, cycloalkylene groups, cycloalkenylene groups, cycloalkynylene groups, alkyl (hetero)arylene groups, (hetero)arylalkylene groups, (hetero)arylalkenylene groups and (hetero)arylalkynylene groups optionally being substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo and silyl groups, wherein the silyl groups can be represented by the formula $(R^4)_3Si$—, wherein $R^4$ is defined as above;

Q is a functional group selected from the group consisting of hydrogen, halogen, $R^6$, —CH=$C(R^6)_2$, —C≡$CR^6$, —$[C(R^6)_2C(R^6)_2O]_Q$—$R^6$, wherein q is in the range of 1 to 200, —CN, —$N_3$, —NCX, —XCN, —$XR^6$, —$N(R^6)_2$, —+$N(R^6)_3$, —$C(X)N(R^6)_2$, —$C(R^6)_2XR^6$, —$C(X)R^6$, —$C(X)XR^6$, —$S(O)R^6$, —$S(O)2R^6$, —$S(O)OR^6$, —$S(O)2OR^6$, —$S(O)N(R^6)_2$, —$S(O)_2N(R^6)_2$, —$OS(O)R^6$, —$OS(O)_2R^6$, —$OS(O)OR^6$, —$OS(O)_2OR^6$, —$P(O)(R^6)(OR^6)$, —$P(O)(OR^6)_2$, —$OP(O)(OR^6)_2$, —$Si(R^6)_3$, —$XC(X)R^6$, —$XC(X)XR^6$, —$XC(X)N(R^6)_2$, —$N(R^6)C(X)R^6$, —$N(R^6)C(X)XR^6$ and —$N(R^6)C(X)N(R^6)_2$, wherein X is oxygen or sulphur;

$R^6$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups; and wherein p is 0 or 1, wherein the spacer unit is represented by formula (IX):

wherein $R^1$, $R^2$, $R^3$ and n are as defined above and

L is selected from the group represented by formula (X):

wherein p is 2 to 5.

11. The process according to claim 9, wherein he spacer unit is represented by formula (XI):

wherein p is 2 to 5.

12. The process according to claim 1, wherein the cell adhesion factor is chosen from a sequence of amino acids that is RGD.

* * * * *